United States Patent
Woodhouse et al.

(10) Patent No.: US 12,365,940 B2
(45) Date of Patent: *Jul. 22, 2025

(54) METHODS OF LABELLING NUCLEIC ACIDS USING VARIABLE LENGTH OLIGONUCLEOTIDES

(71) Applicant: Inivata Ltd., Cambridge (GB)

(72) Inventors: Samuel Woodhouse, Cambridge (GB); Tim Forshew, Stevenage (GB); Stefanie Viola Lensing, Cambridge (GB)

(73) Assignee: Inivata Ltd., Cambridge (GB)

( * ) Notice: Subject to any disclaimer, the term of this patent is extended or adjusted under 35 U.S.C. 154(b) by 187 days.

This patent is subject to a terminal disclaimer.

(21) Appl. No.: 18/313,277

(22) Filed: May 5, 2023

(65) Prior Publication Data

US 2024/0026440 A1 Jan. 25, 2024

Related U.S. Application Data

(63) Continuation of application No. 16/979,129, filed as application No. PCT/IB2019/051866 on Mar. 7, 2019, now Pat. No. 11,674,175.

(30) Foreign Application Priority Data

Mar. 22, 2018 (GB) ..................................... 1804642

(51) Int. Cl.
*C12Q 1/68* (2018.01)
*C12P 19/34* (2006.01)
*C12Q 1/6806* (2018.01)
*C12Q 1/6869* (2018.01)

(52) U.S. Cl.
CPC ......... *C12Q 1/6869* (2013.01); *C12Q 1/6806* (2013.01)

(58) Field of Classification Search
CPC .................................................. C12Q 1/6869
See application file for complete search history.

(56) References Cited

U.S. PATENT DOCUMENTS

| 2015/0299812 | A1* | 10/2015 | Talasaz | .............. | G16B 30/10 |
| 2016/0046986 | A1* | 2/2016 | Eltoukhy | ............ | C12Q 1/6869 |
| | | | | | 435/6.12 |
| 2016/0362748 | A1 | 12/2016 | Mongan et al. | | |
| 2017/0355984 | A1 | 12/2017 | Evans et al. | | |

FOREIGN PATENT DOCUMENTS

| WO | WO 96/06187 A1 | 2/1996 |
| WO | WO 2013/085710 A2 | 6/2013 |
| WO | WO 2013/142389 A1 | 9/2013 |
| WO | WO 2015/134552 A1 | 9/2015 |
| WO | WO 2016/201142 A1 | 12/2016 |
| WO | WO 2018/050722 A1 | 3/2018 |
| WO | WO 2018/217625 A1 | 11/2018 |
| WO | WO-2019180528 A1 | 9/2019 |

OTHER PUBLICATIONS

Plagnol et al., "Analytical validation of a next generation sequencing liquid biopsy assay for high sensitivity broad molecular profiling", PLoS One, 2018, 13(3): e0193802.
Bodi, Kip et al. Comparison of commercially available target enrichment methods for next-generation sequencing. Journal of biomolecular techniques 24(2):73-86 (2013).
Depristo, Mark A. et al. A framework for variation discovery and genotyping using next-generation DNA sequencing data. Nature genetics 43(5):491-498 (2011).
Fonseca, Nuno A. et al. Tools for mapping high-throughput sequencing data. Bioinformatics 28(24):3169-3177 (2012).
Forshew, Tim et al. Noninvasive identification and monitoring of cancer mutations by targeted deep sequencing of plasma DNA. Science Translational Medicine 4(136):136ra68, 1-12 (2012).
Gnirke, Andreas et al. Solution Hybrid Selection with Ultra-Long Oligonucleotides for Massively Parallel Targeted Sequencing. Nature Biotechnology 27(2):182-189 (2009).
Goodwin, Sara et al. Coming of age: ten years of next-generation sequencing technologies. Nature Reviews Genetics 17(6): 333-351 (2016).
Lin, P. Kong Thoo, and Daniel M. Brown. Synthesis and duplex stability of oligonucleotides containing cytosine-thymine analogues. Nucleic acids research 17(24):10373-10383 (1989).
Lin, Paul Kong Thoo, and Daniel M. Brown. Synthesis of oligodeoxyribonucleotides containing degenerate bases and their use as primers in the polymerase chain reaction. Nucleic acids research 20(19):5149-5152 (1992).
Loakes, David. et al. Evolving a polymerase for hydrophobic base analogues. Journal of the American Chemical Society 131(41):14827-14837 (2009).
Loakes, David. Survey and Summary: The applications of universal DNA base analogues. Nucleic Acids Research 29(12):2437-2447 (2001).
Mamanova, Lira. et al. Target-enrichment strategies for next-generation sequencing. Nature methods 7(2):111-118 (2010).
PCT/IB2019/051866 International Search Report and Written Opinion dated May 14, 2019.

* cited by examiner

*Primary Examiner* — Kenneth R Horlick
(74) *Attorney, Agent, or Firm* — Wilson Sonsini Goodrich & Rosati

(57) ABSTRACT

A method of labelling a nucleic acid of interest (NAOI) is provided. In some embodiments, the method may comprise contacting a sample comprising the nucleic acid of interest with a pool of oligonucleotides, the pool comprising oligonucleotides having at least 5 different lengths; and attaching an oligonucleotide from the pool on to one or each end of the nucleic acid of interest, wherein attachment of an oligonucleotide moves the read start and/or stop coordinate when the labelled NAOI is sequenced.

20 Claims, 7 Drawing Sheets

Specification includes a Sequence Listing.

A

B

```
>Annealed Adapter (2bp region underlined)
5'-ACACTCTTTCCCTACACGACGCTCTTCCGATCTAGGCAAT-3'
                                   ||||||||||||||||||||
3'- CTGACCTCAAGTCTGCACACGAGAAGGCTAGTCCGTT-P5
                                    ---

>Annealed Adapter (3bp region underlined)
5'-ACACTCTTTCCCTACACGACGCTCTTCCGATCTAGGCAAT-3'
                                  |||||||||||||||||||||
3'- CTGACCTCAAGTCTGCACACGAGAAGGCTAGATCCGTT-P5
                                    ----

>Annealed Adapter (4bp region underlined)
5'-ACACTCTTTCCCTACACGACGCTCTTCCGATCTAGGCAAT-3'
                                 ||||||||||||||||||||||
3'- CTGACCTCAAGTCTGCACACGAGAAGGCTAGATCCGTT-P5
                                    -----

>Annealed Adapter (5bp region underlined)
5'-ACACTCTTCCCTACACGACGCTCTTCCGATCTAGGCAAT-3'
                                ||||||||||||||||||||||
3'- CTGACCTCAAGTCTGCACACGAGAAGGCTAGATCCGTT-P5
                                    ------

>Ligation product (5bp and 2bp)
ACACTCTTTCCCTACACGACGCTCTTCCGATCGCTAGGCAATXXXXXXXXXATTGCCTGATCGGAAGAGCACACGTCTGAACTCCAGTC
                                          |||||||||||||||||||||||||||||||||||||||||||||||||
         CTGACCTCAAGTCGGCACACGAGAAGGCTAGCGATCCGTTAXXXXXXXXXXTAACGGACTAGCTCTCGCAGCACATCCCCTTCTCACA >i5 PCR primer
5'-AATGATACGGCGACCACCGAGATCTACAC[i5]ACACTCTTTCCCTACACGACGCTCTTCCGATCT-3'

>i7 PCR primer
5'-CAAGCAGAAGACGGCATACGAGAT[i7]GTGACTGGAGTTCAGACGTGTGCTCTTCCGATCT-3'

>PCR product
5'-AATGATACGGCGACCACCGAGATCTACAC[i5]ACACTCTTCCCTACACGACGCTCTTCCGATCTXXXX...       XXXXAGATCGGAAGAGCACACGTCTGAACTCCAGTCAC[i7]atctcgtatgccgtcttctgcttg-3'
3'-ttactatgccgctggtggctctagatgtg[i5]TGTGAGAAGGGGATGTGCTGCGAGAAGGCTAGAXXXX...       XXXXTTCTAGCCTTCTCCGTGTGCAGACTTGAGGTCAGTG[i7]TAGAGCATACGGCCAGAAGACGAAC-5'
```

FIG. 7

SEQUENCE LISTING

```
Sequence total quantity: 33
SEQ ID NO: 1             moltype = DNA  length = 70
FEATURE                  Location/Qualifiers
misc_feature             1..70
                         note = synthetic sequence
misc_feature             69..70
                         note = A phosphorothioate linkage is present between the
                           nucleotides at positions 69 to 70.
source                   1..70
                         mol_type = other DNA
                         organism = synthetic construct
SEQUENCE: 1
aatgatacgg cgaccaccga gatctacact atagcctaca ctctttccct acacgacgct   60
cttccgatct                                                          70

SEQ ID NO: 2             moltype = DNA  length = 66
FEATURE                  Location/Qualifiers
misc_feature             1..66
                         note = synthetic sequence
misc_feature             65..66
```

```
                           note = A phosphorothioate linkage is present between the
                             nucleotides at positions 65 and 66
source                     1..66
                           mol_type = other DNA
                           organism = synthetic construct
SEQUENCE: 2
caagcagaag acggcatacg agatcgagta atgtgactgg agttcagacg tgtgctcttc    60
cgatct                                                               66

SEQ ID NO: 3               moltype = DNA  length = 55
FEATURE                    Location/Qualifiers
misc_feature               1..55
                           note = synthetic sequence
misc_difference            34
                           note = n is a, c, g, or t
misc_feature               54..55
                           note = A phosphorothioate linkage is present between the
                             nucleotides at positions 54 and 55.
source                     1..55
                           mol_type = other DNA
                           organism = synthetic construct
SEQUENCE: 3
acactctttc cctacacgac gctcttccga tctngcatta cagctkcgkg tacgt         55

SEQ ID NO: 4               moltype = DNA  length = 55
FEATURE                    Location/Qualifiers
misc_feature               1..55
                           note = synthetic sequence
misc_difference            23
                           note = n is a, c, g, or t
source                     1..55
                           mol_type = other DNA
                           organism = synthetic construct
SEQUENCE: 4
cgtactcagc aagctgtaat gcnagatcgg aagagcacac gtctgaactc cagtc         55

SEQ ID NO: 5               moltype = DNA  length = 46
FEATURE                    Location/Qualifiers
misc_feature               1..46
                           note = synthetic sequence
misc_difference            34
                           note = n is a, c, g, or t
misc_feature               45..46
                           note = A phosphorothioate linkage is present between the
                             nucleotides at positions 45 and 46.
source                     1..46
                           mol_type = other DNA
                           organism = synthetic construct
SEQUENCE: 5
acactctttc cctacacgac gctcttccga tctnctkcgk gtacgt                   46

SEQ ID NO: 6               moltype = DNA  length = 46
FEATURE                    Location/Qualifiers
misc_feature               1..46
                           note = synthetic sequence
misc_difference            14
                           note = n is a, c, g, or t
source                     1..46
                           mol_type = other DNA
                           organism = synthetic construct
SEQUENCE: 6
cgtactcagc aagnagatcg gaagagcaca cgtctgaact ccagtc                   46

SEQ ID NO: 7               moltype = DNA  length = 54
FEATURE                    Location/Qualifiers
misc_feature               1..54
                           note = synthetic sequence
misc_feature               53..54
                           note = A phosphorothioate linkage is present between the
                             nucleotides at positions 53 and 54.
source                     1..54
                           mol_type = other DNA
                           organism = synthetic construct
SEQUENCE: 7
acactctttc cctacacgac gctcttccga tctgcattac agctkcgkgt acgt          54

SEQ ID NO: 8               moltype = DNA  length = 54
FEATURE                    Location/Qualifiers
misc_feature               1..54
```

```
                        note = synthetic sequence
source                  1..54
                        mol_type = other DNA
                        organism = synthetic construct
SEQUENCE: 8
cgtactcagc aagctgtaat gcagatcgga agagcacacg tctgaactcc agtc        54

SEQ ID NO: 9            moltype = DNA   length = 45
FEATURE                 Location/Qualifiers
misc_feature            1..45
                        note = synthetic sequence
misc_feature            44..45
                        note = A phosphorothioate linkage is present between the
                         nucleotides at positoins 44 and 45.
source                  1..45
                        mol_type = other DNA
                        organism = synthetic construct
SEQUENCE: 9
acactctttc cctacacgac gctcttccga tctctkcgkg tacgt                  45

SEQ ID NO: 10           moltype = DNA   length = 45
FEATURE                 Location/Qualifiers
misc_feature            1..45
                        note = synthetic sequence
source                  1..45
                        mol_type = other DNA
                        organism = synthetic construct
SEQUENCE: 10
cgtactcagc aagagatcgg aagagcacac gtctgaactc cagtc                  45

SEQ ID NO: 11           moltype = DNA   length = 21
FEATURE                 Location/Qualifiers
misc_feature            1..21
                        note = synthetic sequence
source                  1..21
                        mol_type = other DNA
                        organism = synthetic construct
SEQUENCE: 11
tagcatgcag ccgtacatga g                                            21

SEQ ID NO: 12           moltype = DNA   length = 21
FEATURE                 Location/Qualifiers
misc_feature            1..21
                        note = synthetic sequence
source                  1..21
                        mol_type = other DNA
                        organism = synthetic construct
SEQUENCE: 12
gtagcatgca gccgtacatg a                                            21

SEQ ID NO: 13           moltype = DNA   length = 21
FEATURE                 Location/Qualifiers
misc_feature            1..21
                        note = synthetic sequence
source                  1..21
                        mol_type = other DNA
                        organism = synthetic construct
SEQUENCE: 13
gtagcatgct gccgtacatg a                                            21

SEQ ID NO: 14           moltype = DNA   length = 18
FEATURE                 Location/Qualifiers
misc_feature            1..18
                        note = synthetic sequence
source                  1..18
                        mol_type = other DNA
                        organism = synthetic construct
SEQUENCE: 14
gcatgcagcc gtacatga                                                18

SEQ ID NO: 15           moltype = DNA   length = 18
FEATURE                 Location/Qualifiers
misc_feature            1..18
                        note = synthetic sequence
source                  1..18
                        mol_type = other DNA
                        organism = synthetic construct
SEQUENCE: 15
gcatgctgcc gtacatga                                                18
```

```
SEQ ID NO: 16              moltype = DNA   length = 19
FEATURE                    Location/Qualifiers
misc_feature               1..19
                           note = synthetic sequence
source                     1..19
                           mol_type = other DNA
                           organism = synthetic construct
SEQUENCE: 16
gcatgcagcc gtacatgag                                                  19

SEQ ID NO: 17              moltype = DNA   length = 29
FEATURE                    Location/Qualifiers
misc_feature               1..29
                           note = synthetic sequence
source                     1..29
                           mol_type = other DNA
                           organism = synthetic construct
SEQUENCE: 17
gaggcgcatg cagccgtaca tgagacagt                                       29

SEQ ID NO: 18              moltype = DNA   length = 39
FEATURE                    Location/Qualifiers
misc_feature               1..39
                           note = synthetic sequence
source                     1..39
                           mol_type = other DNA
                           organism = synthetic construct
SEQUENCE: 18
acactctttc cctacacgac gctcttccga tcaggcaat                             39

SEQ ID NO: 19              moltype = DNA   length = 37
FEATURE                    Location/Qualifiers
misc_feature               1..37
                           note = synthetic sequence
source                     1..37
                           mol_type = other DNA
                           organism = synthetic construct
SEQUENCE: 19
ttgcctgatc ggaagagcac acgtctgaac tccagtc                              37

SEQ ID NO: 20              moltype = DNA   length = 40
FEATURE                    Location/Qualifiers
misc_feature               1..40
                           note = synthetic sequence
source                     1..40
                           mol_type = other DNA
                           organism = synthetic construct
SEQUENCE: 20
acactctttc cctacacgac gctcttccga tctaggcaat                            40

SEQ ID NO: 21              moltype = DNA   length = 38
FEATURE                    Location/Qualifiers
misc_feature               1..38
                           note = synthetic sequence
source                     1..38
                           mol_type = other DNA
                           organism = synthetic construct
SEQUENCE: 21
ttgcctagat cggaagagca cacgtctgaa ctccagtc                             38

SEQ ID NO: 22              moltype = DNA   length = 41
FEATURE                    Location/Qualifiers
misc_feature               1..41
                           note = synthetic sequence
source                     1..41
                           mol_type = other DNA
                           organism = synthetic construct
SEQUENCE: 22
acactctttc cctacacgac gctcttccga tcctaggcaa t                         41

SEQ ID NO: 23              moltype = DNA   length = 39
FEATURE                    Location/Qualifiers
misc_feature               1..39
                           note = synthetic sequence
source                     1..39
                           mol_type = other DNA
                           organism = synthetic construct
SEQUENCE: 23
```

```
ttgcctagga tcggaagagc acacgtctga actccagtc                          39

SEQ ID NO: 24           moltype = DNA   length = 42
FEATURE                 Location/Qualifiers
misc_feature            1..42
                        note = synthetic sequence
source                  1..42
                        mol_type = other DNA
                        organism = synthetic construct
SEQUENCE: 24
acactctttc cctacacgac gctcttccga tcgctaggca at                      42

SEQ ID NO: 25           moltype = DNA   length = 40
FEATURE                 Location/Qualifiers
misc_feature            1..40
                        note = synthetic sequence
source                  1..40
                        mol_type = other DNA
                        organism = synthetic construct
SEQUENCE: 25
ttgcctagcg atcggaagag cacacgtctg aactccagtc                         40

SEQ ID NO: 26           moltype = DNA   length = 86
FEATURE                 Location/Qualifiers
misc_feature            1..86
                        note = synthetic sequence
misc_difference         43..48
                        note = n is a, c, g, or t
source                  1..86
                        mol_type = other DNA
                        organism = synthetic construct
SEQUENCE: 26
acactctttc cctacacgac gctcttccga tcgctaggca atnnnnnnat tgcctgatcg   60
gaagagcaca cgtctgaact ccagtc                                        86

SEQ ID NO: 27           moltype = DNA   length = 86
FEATURE                 Location/Qualifiers
misc_feature            1..86
                        note = synthetic sequence
misc_difference         40..45
                        note = n is a, c, g, or t
source                  1..86
                        mol_type = other DNA
                        organism = synthetic construct
SEQUENCE: 27
acactctttc cctacacgac gctcttccga tcaggcaatn nnnnattgc ctagcgatcg    60
gaagagcaca cgtctgaact ccagtc                                        86

SEQ ID NO: 28           moltype = DNA   length = 62
FEATURE                 Location/Qualifiers
misc_feature            1..62
                        note = synthetic sequence
misc_feature            29..30
                        note = i5 is present between the nucleotides at positoin 29
                         and 30
source                  1..62
                        mol_type = other DNA
                        organism = synthetic construct
SEQUENCE: 28
aatgatacgg cgaccaccga gatctacaca cactctttcc ctacacgacg ctcttccgat   60
ct                                                                  62

SEQ ID NO: 29           moltype = DNA   length = 58
FEATURE                 Location/Qualifiers
misc_feature            1..58
                        note = synthetic sequence
misc_feature            24..25
                        note = i7 is present between the nucleotides at positoins
                         24 and 25.
source                  1..58
                        mol_type = other DNA
                        organism = synthetic construct
SEQUENCE: 29
caagcagaag acggcatacg agatgtgact ggagttcaga cgtgtgctct tccgatct     58

SEQ ID NO: 30           moltype = DNA   length = 66
FEATURE                 Location/Qualifiers
misc_feature            1..66
                        note = synthetic sequence
```

```
misc_feature          29..30
                         note = i5 is present between the nucleotides at positions
                         29 and 30.
misc_difference       63..66
                         note = n is a, c, g, or t
source                1..66
                         mol_type = other DNA
                         organism = synthetic construct
SEQUENCE: 30
aatgatacgg cgaccaccga gatctacaca cactctttcc ctacacgacg ctcttccgat    60
ctnnnn                                                               66

SEQ ID NO: 31         moltype = DNA  length = 66
FEATURE               Location/Qualifiers
misc_feature          1..66
                         note = synthetic sequence
misc_difference       1..4
                         note = n is a, c, g, or t
misc_feature          37..38
                         note = I5 is present between the nucleotides at positions
                         37 and 38
source                1..66
                         mol_type = other DNA
                         organism = synthetic construct
SEQUENCE: 31
nnnnagatcg gaagagcgtc gtgtagggaa agagtgtgtg tagatctcgg tggtcgccgt    60
atcatt                                                               66

SEQ ID NO: 32         moltype = DNA  length = 62
FEATURE               Location/Qualifiers
misc_feature          1..62
                         note = synthetic sequence
misc_difference       1..4
                         note = n is a, c, g, or t
misc_feature          38..39
                         note = i7 is present between the nucleotides at positoins
                         38 and 39
source                1..62
                         mol_type = other DNA
                         organism = synthetic construct
SEQUENCE: 32
nnnnagatcg gaagagcaca cgtctgaact ccagtcacat ctcgtatgcc gtcttctgct    60
tg                                                                   62

SEQ ID NO: 33         moltype = DNA  length = 62
FEATURE               Location/Qualifiers
misc_feature          1..62
                         note = synthetic sequence
misc_feature          24..25
                         note = i7 is present between the nucleotides at positoins
                         24 and 25.
misc_difference       59..62
                         note = n is a, c, g, or t
source                1..62
                         mol_type = other DNA
                         organism = synthetic construct
SEQUENCE: 33
caagcagaag acggcatacg agatgtgact ggagttcaga cgtgtgctct tccgatctnn    60
nn                                                                   62
```

METHODS OF LABELLING NUCLEIC ACIDS USING VARIABLE LENGTH OLIGONUCLEOTIDES

CROSS-REFERENCING

This application is a continuation of U.S. application Ser. No. 16/979,129, filed on Sep. 8, 2020, and issued as U.S. Pat. No. 11,674,175 on Jun. 13, 2023, which is a § 371 national phase of International Application No. PCT/IB/2019/051866, filed on Mar. 7, 2019, which claims the benefit of United Kingdom Patent Application Serial No. GB1804642.5, filed on Mar. 22, 2018, all of which applications are incorporated by reference herein.

INCORPORATION BY REFERENCE OF SEQUENCE LISTING PROVIDED AS A SEQUENCE LISTING XML FILE

A Sequence Listing is provided herewith as a Sequence Listing XML, "INIV-007CON_SEQ_LIST", created on May 5, 2023 and having a size of 52,635 bytes. The contents of the Sequence Listing XML are incorporated herein by reference in their entirety.

BACKGROUND

Next-generation sequencing (NGS) and library preparation has inherent error and amplification biases, meaning the ability to detect mutations/variants at an allele frequency of 1% or below is challenging. Several methods have been proposed to overcome these limitations. Tagging of NGS libraries with molecular barcodes has been used to detect NGS errors, these methods employ a fixed length of degenerate (mixed) bases coupled to sequencing adaptors that generate a high number of different tags, typically >100,000 possible combinations. The number of different tags present after sequencing can be used to estimate the number of different polynucleotides present initially. Molecular barcodes are synthesized as single-stranded oligonucleotides and can be attached by PCR, ligation or primer extension. To ensure that each nucleic acid present in a sample is labelled with a unique molecular barcode, it is necessary to generate a highly complex mix of barcodes, which can be a costly and time-consuming process that requires separate barcode synthesis reactions and pooling of tags (WO2013142389). A low diversity tag of fixed length leads to inefficient sequencing as NGS/Illumina phasing calculations cannot be made, therefore a high degree of tag diversity is required. Further methods of identifying errors involve splitting the sample into multiple replicate processing steps and identifying changes that have occurred across multiple reactions. However, splitting the reaction increases costs, complexity and in some circumstances, decreases assay sensitivity. Additionally, PCR/NGS generates errors based on sequence context and thus errors are not entirely random, this can lead to consistent errors within a given sequence. Bioinformatics tools trained on control sample sets can be used to filter out consistent NGS error, however they cannot account for random errors introduced by NGS processing, e.g., by PCR. In the above methods, an error introduced during the first copy/amplification of a nucleic acid of interest (NAOI) will be propagated through the reaction and could be identified as a "true" variant/alteration, even though it was an error that occurred during the PCR.

The start and end co-ordinates of a molecule can be used as unique molecular identifiers. The non-random nature of ctDNA fragmentation and the limited number of break-point combinations may not allow a suitable level of detection when only breakpoints are used. Molecular barcoding could be used to increase diversity. However, there remains a need in the art for a method of labelling, identifying and stratifying nucleic acids to allow detection of low allelic frequency mutations in patient samples. The present invention provides such methods.

SUMMARY OF THE INVENTION

In a first aspect of the invention there is provided a method of labelling a nucleic acid of interest (NAOI), comprising:
  contacting a sample comprising the nucleic acid of interest with a pool of oligonucleotides, the pool comprising oligonucleotides having at least 5 different lengths; and
  attaching an oligonucleotide from the pool on to one or each end of the nucleic acid of interest, wherein attachment of an oligonucleotide moves the read start and/or stop coordinate when the labelled NAOI is sequenced.

In a second aspect of the invention, there is provided a method of labelling a nucleic acid of interest (NAOI), comprising
  a) providing a sample comprising a plurality of NAOIs, each having a natural start coordinate defined by the 5' end of the NAOI and a natural stop coordinate defined by the 3' end of the NAOI;
  b) contacting the sample with a pool of oligonucleotides, the pool comprising oligonucleotides having at least 5 different lengths;
  c) attaching an oligonucleotide from the pool to one or each end of a plurality of NAOIs to provide a plurality of labelled NAOIs, wherein attachment of the oligonucleotides to the plurality of NAOIs alters the number of base pairs of the NAOI that are obtained when the labelled NAOI is subsequently sequenced;
  d) amplifying the labelled NAOIs;
  e) sequencing the labelled NAOIs to provide a library of reads;
  f) grouping the reads according to the sequence obtained from the NAOI;
  g) determining a consensus sequence for each NAOI.

In a third aspect of the invention there is provided a pool of oligonucleotides having at least 5 different lengths, wherein each oligonucleotide comprises a universal priming site (UPS), a spacer region, a filler region and a ligation moiety. The oligonucleotides may comprise the other features of the oligonucleotides as described herein, such as a PCR cycle counter generator.

In a fourth aspect of the invention, there is provided a method of sequencing a NAOI, the method comprising the steps of:
  a. providing a sample from a patient, said sample comprising a plurality of NAOIs, wherein the NAOIs are cell-free DNA (cfDNA) molecules;
  b. labelling a plurality of the NAOIs according to a method of the invention as described herein; and
  c. sequencing the labelled NAOIs.

In another aspect of the invention there is provided a method of diagnosing cancer, comprising:
  a. providing a sample from a patient, said sample comprising cell free (cfDNA) molecules;
  b. determining the sequence of one or more of the cfDNA molecules according a method of the invention as described herein;

c. determining the presence or absence of one or more genetic alterations in the cfDNA molecules; and
d. determining the presence or absence of cancer based on the presence or absence of the one or more genetic alterations.

In another aspect of the invention there is provided a method of determining cancer remission or relapse, comprising:
a. providing a sample from a patient, said sample comprising a plurality of cfDNA molecules;
b. determining the sequence of one or more cfDNA molecules according to a method of the invention;
c. determining the presence or absence of one or more genetic alterations in the cfDNA molecules; and
d. determining cancer remission or relapse based on the absence or presence of the one or more genetic alterations.

In another aspect of the invention there is provided a method of detecting progression of cancer, comprising:
a. providing a sample from a patient, said sample comprising a plurality of cfDNA molecules;
b. determining the sequence of one or more of the cfDNA molecules according to a method of the invention as described herein;
c. determining the presence or absence of one or more genetic alterations in the cfDNA molecules, or determining a change in the abundance of the one or more genetic alterations;
d. optionally comparing the results from step (c) to the results for the same patient using a sample obtained at a previous point in time; and
e. determining a progression of cancer based on the presence or absence of the one or more genetic alterations, or based on a change in the abundance of the one of more genetic alterations.

In another aspect of the invention there is provided a method of determining the presence of residual cancer, comprising:
a. providing a sample from a patient, said sample comprising a plurality of cfDNA molecules;
b. determining the sequence of one or more of the cfDNA molecules according to a method of the invention as described herein;
c. determining the presence or absence of one or more genetic alterations in the cfDNA molecules; and
d. determining the presence of residual cancer based on the presence or absence of the one or more genetic alterations.

In a further aspect of the invention there is provided a method of stratifying a microbial population, comprising:
a. obtaining a sample comprising a plurality of microbial nucleic acids of interest;
b. determining the sequence of one or more of the microbial nucleic acids of interest according to a method of the invention as described herein;
c. mapping the sequence reads obtained in step b to a reference genome or genomes; and
d. stratifying the microbial population according to the identified microbes.

In a further aspect of the invention there is provided a method of treating cancer, comprising
a. providing a sample from a patient, said sample comprising one or more cell-free nucleic acid molecules;
b. determining the sequence of one or more of the cell-free nucleic acid molecules according to a method of the invention as described herein;
c. determining the presence or absence of a genetic alteration in the cell-free nucleic acid molecules;
d. selecting a cancer treatment regimen for the patient according to the presence or absence of a genetic alteration in the one or more cell-free nucleic acid molecules; and
e. administering said treatment to the patient.

In a further aspect of the invention there is provided a method of selecting a treatment regimen for a cancer patient or a patient suspected of having cancer, comprising:
a. providing a sample from a patient, said sample comprising one or more cell-free nucleic acid molecules;
b. determining the sequence of one or more of the cell-free nucleic acid molecules according to a method of the invention as described herein;
c. determining the presence or absence of a genetic alteration in the cell-free nucleic acid molecules; and
d. selecting a cancer treatment regimen for the patient according to the presence or absence of a genetic alteration in the cell-free nucleic acid molecules.

In a further aspect of the invention there is provided a method of predicting a patient's responsiveness to a cancer treatment, comprising
a. providing a sample from a patient, said sample comprising a plurality of cell-free DNA (cfDNA) molecules;
b. determining the sequence of one or more of the cfDNA molecules according to a method of the invention as described herein;
c. determining the presence or absence of a genetic alteration in the cell-free nucleic acid molecules; and
d. predicting a patient's responsiveness to a cancer treatment according to the presence or absence of a genetic alteration.

In a further aspect of the invention there is provided a mixture or composition comprising a plurality of adaptors of the invention, and one or more nucleic acids of interest.

In a further aspect of the invention there is provided a kit of parts comprising one or more adaptors of the invention and instructions for use.

BRIEF DESCRIPTION OF THE DRAWINGS

The skilled artisan will understand that the drawings, described below, are for illustration purposes only. The drawings are not intended to limit the scope of the present teachings in any way.

FIGS. 7—5 example adaptors of the invention having 2, 3, 4 or 5 base pair spacer sequences. The example adaptors comprise Illumina i5 and i7 sequences and are ligated to the NAOI. The resulting PCR product is shown. The sequences from top to bottom are set forth in SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33.

DETAILED DESCRIPTION

Figure 1:
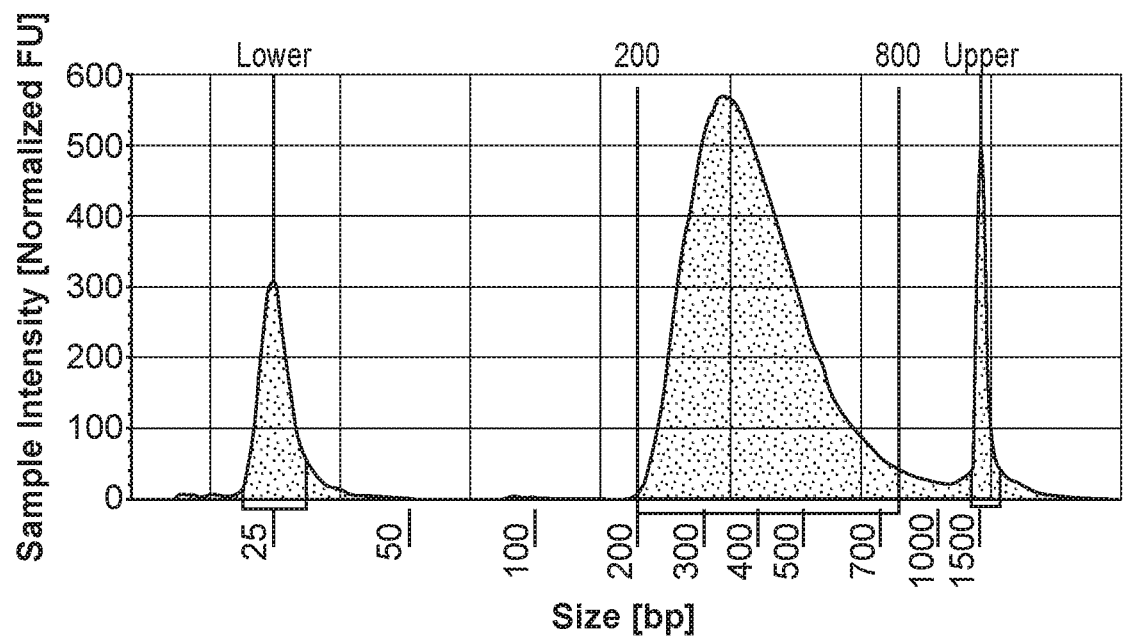
FIG. 1—Adapter ligated DNA, that has been amplified and will serve as input into the enrichment reaction (hybridization). Gel electrophoresis (tapestation) peak profile showing size distribution and abundance of DNA; whereby size is displayed on the x axis (base pairs) and abundance is displayed on the y axis (intensity).
Figure 2:
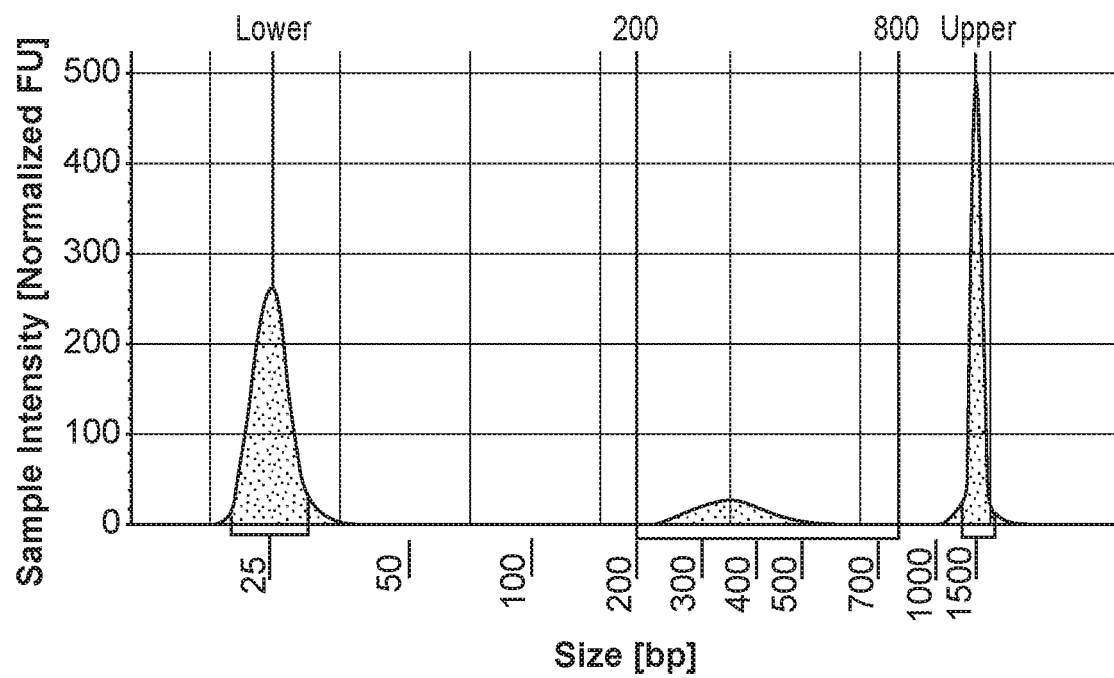
FIG. 2—DNA following region-specific enrichment with hybridization. Gel electrophoresis (tapestation) peak profile showing size distribution and abundance of DNA; whereby size is displayed on the x axis (base pairs) and abundance is displayed on the y axis (intensity).
Figure 3:
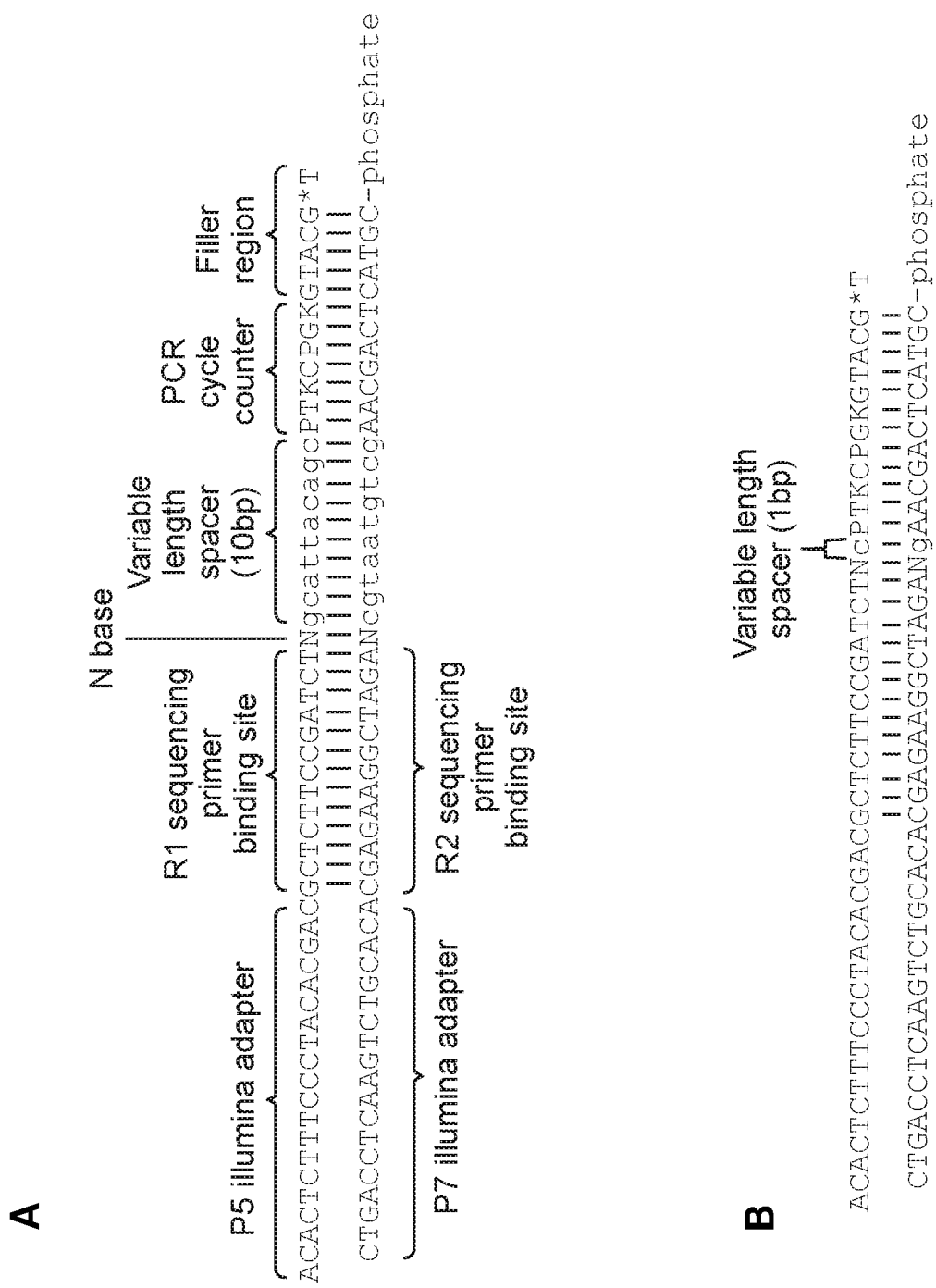
FIG. 3—A ligation adapter (a) adapter with 10 bp variable length sequence and (b) adapter with 1 bp variable length sequence, with an additional "N" base to inhibit intramolecule secondary structure formation (e.g. hairpins). Panel A top strand: (SEQ ID NO: 3); Panel A bottom strand: (SEQ ID NO:4); Panel B top strand: (SEQ ID NO: 5); Panel B bottom strand: (SEQ ID NO: 6).
Figure 4:
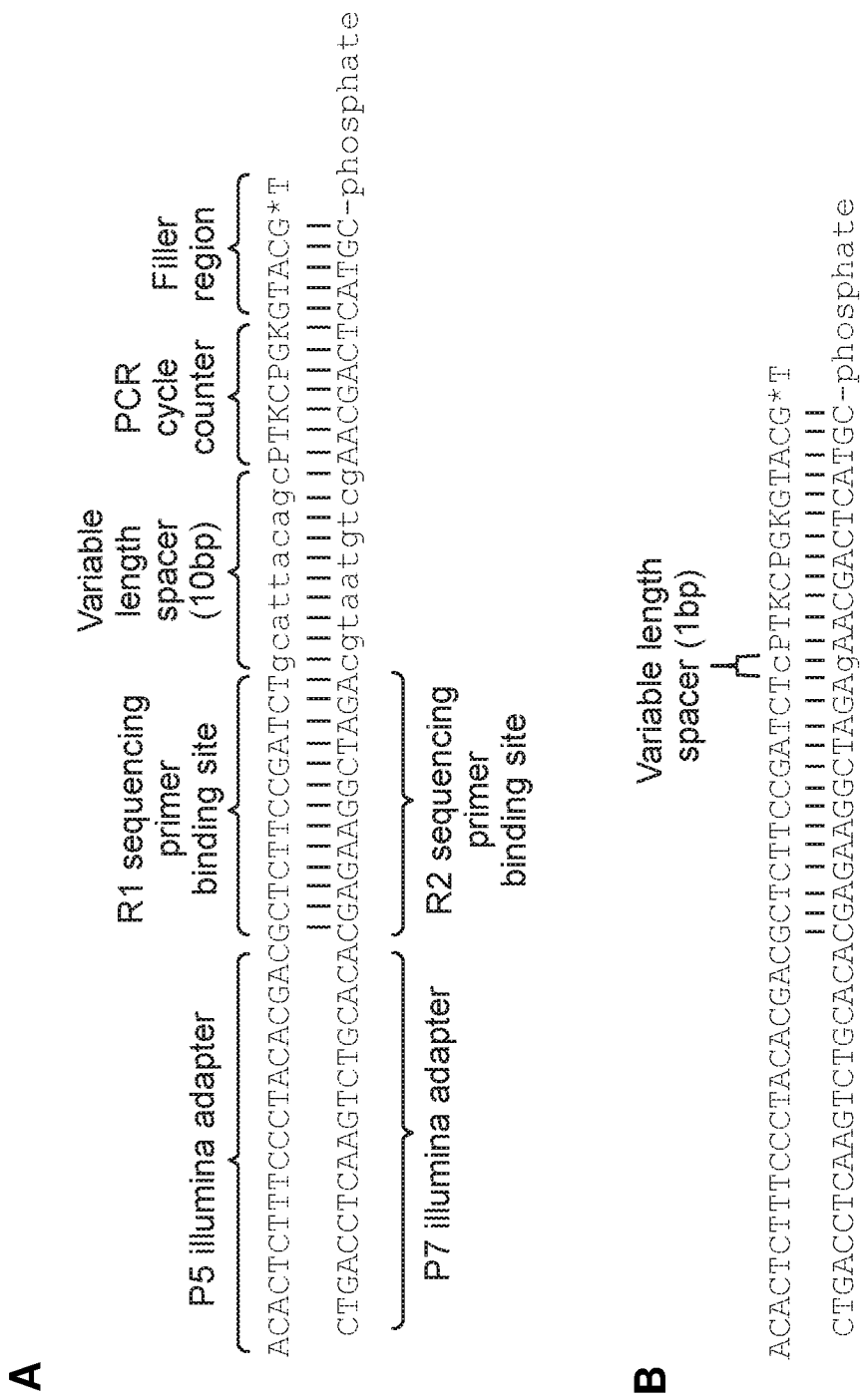
FIG. 4—A ligation adapter (a) adapter with 10 bp variable length sequence and (b) adapter with 1 bp variable length sequence. Panel A top strand: (SEQ ID NO: 7); Panel A bottom strand: (SEQ ID NO: 8); Panel B top strand: (SEQ ID NO: 9); Panel B bottom strand: (SEQ ID NO: 10).
Figure 5:
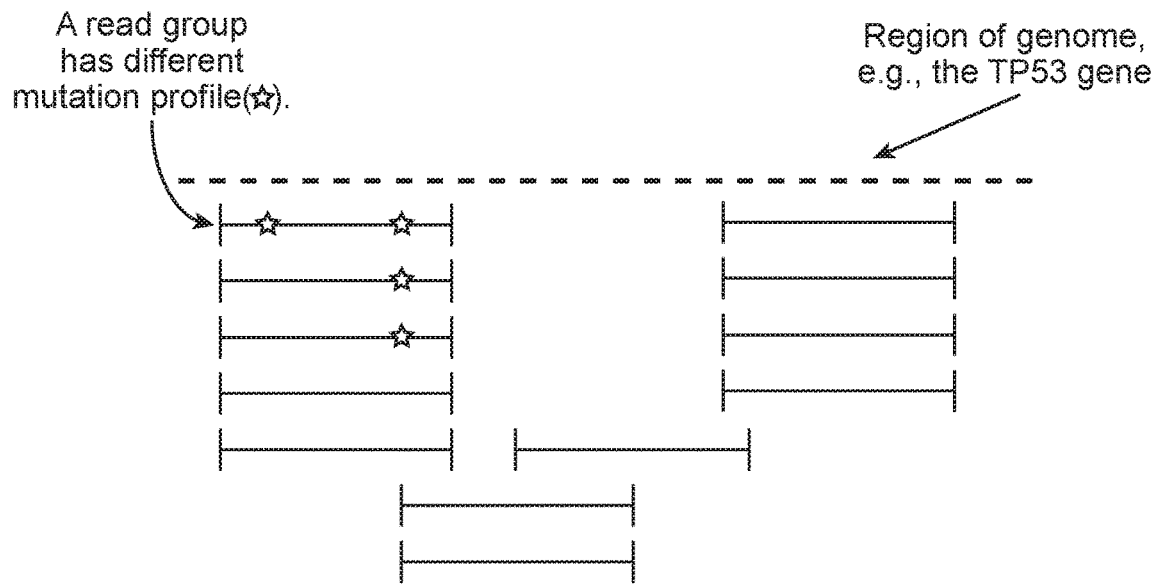
FIG. 5—Example analysis of sequence reads to correct for errors introduced during the processing of the NAOI. In A, paired end reads are aligned to the genome based on start and end coordinate of the starting fragmented molecule (i.e., the natural start and end co-ordinate). In B, reads are grouped together based on start and end coordinates of Read 1 (RD1) and Read 2 (RD2). Length of Read adapters determines the length of the read mapping to the genomic region. A change of 1 bp can be detected by Illumina sequencing. This is the synthetic start and end coordinate. In C, molecules sharing the same natural start and end co-ordinate and synthetic start and end co-ordinate are used to generate a consensus sequence. In this example three molecules were identified and an error introduced during PCR was removed.
Figure 5:
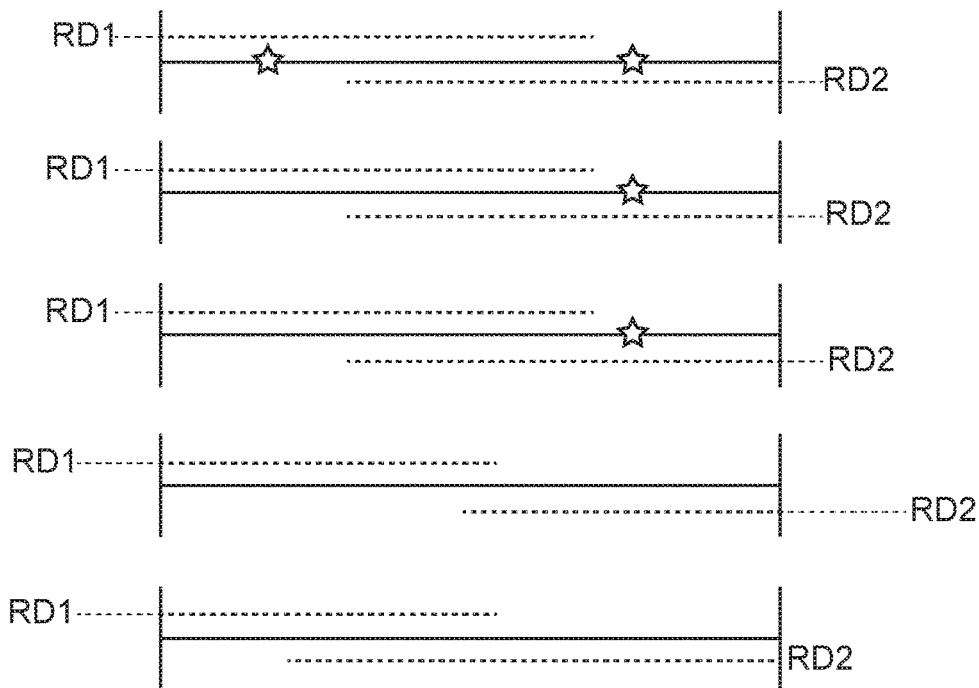
Figure 5:
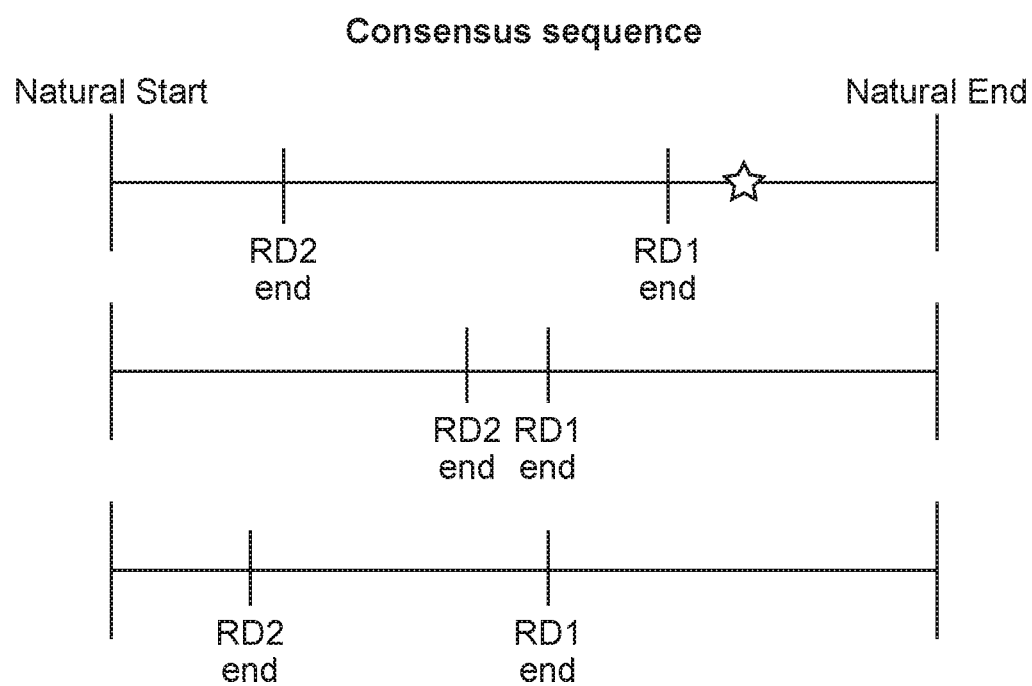
Figure 6:
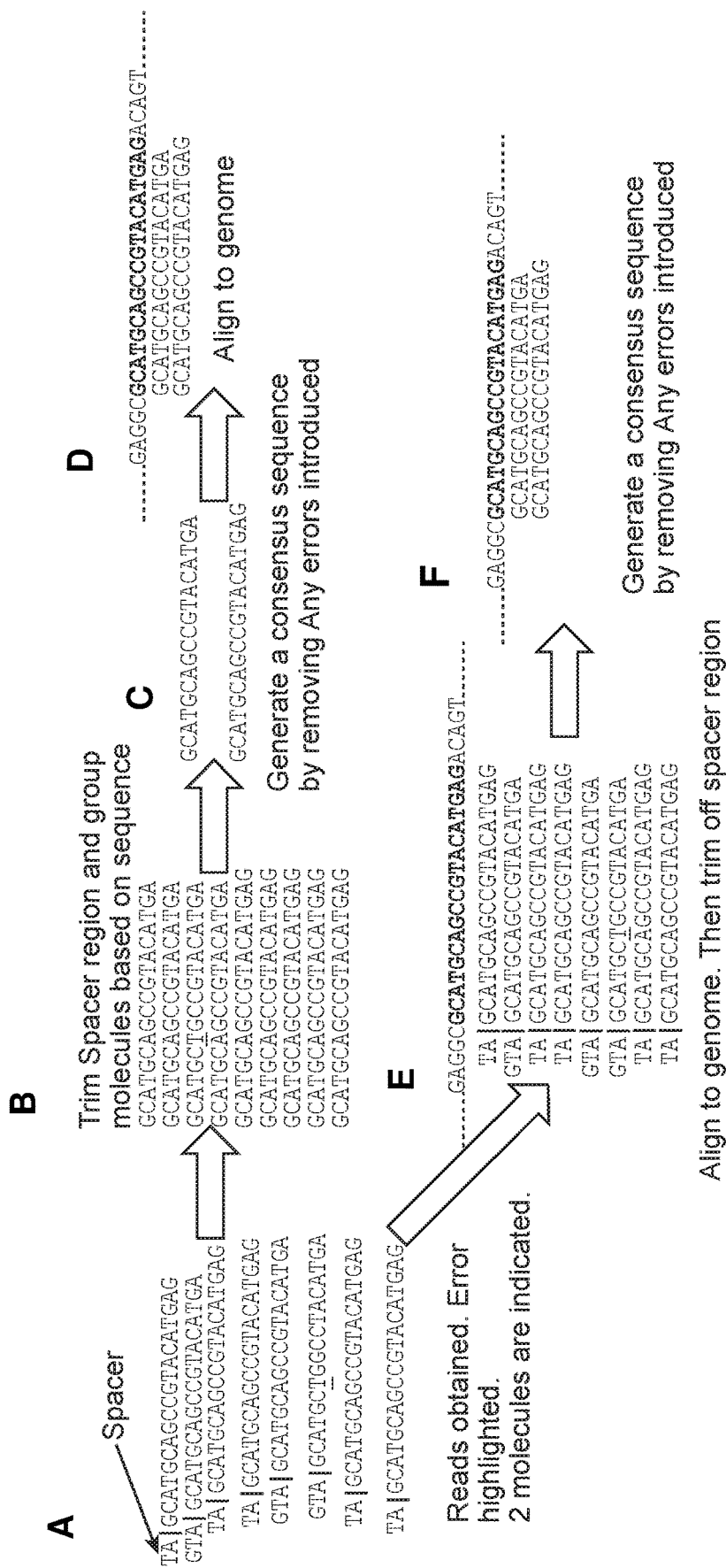
FIG. 6—Two example analyses of sequence reads to correct for errors introduced during the processing of the NAOI. In the upper example, the spacer sequences are trimmed off the sequence reads before generating a consensus sequence and aligning to a genome. In the lower example, the sequence reads are aligned to the genome first, before removing the spacers and generate a consensus sequence by removing errors. Panel A from top to bottom: SEQ ID NO: 11, SEQ ID NO: 12, SEQ ID NO: 11, SEQ ID NO: 11, SEQ ID NO: 12, SEQ ID NO: 13, SEQ ID NO: 11, SEQ ID NO: 11; Panel B from top to bottom: SEQ ID NO: 14, SEQ ID NO: 14, SEQ ID NO: 15, SEQ ID NO: 14, SEQ ID NO: 16, SEQ ID NO: 16, SEQ ID NO: 16, SEQ ID NO: 16, SEQ ID NO: 16; Panel C from top to bottom: SEQ ID NO: 14, SEQ ID NO: 16; Panel D from top to bottom: SEQ ID NO: 17, SEQ ID NO: 14, SEQ ID NO: 16; Panel E from to bottom: SEQ ID NO: 17, SEQ ID NO: 11, SEQ ID NO:12, SEQ ID NO: 11, SEQ ID NO: 11, SEQ ID NO: 12, SEQ ID NO: 13, SEQ ID NO: 11, SEQ ID NO: 11; Panel F from top to bottom: SEQ ID NO:17, SEQ ID NO:14, SEQ ID NO: 16).

When undertaking a liquid biopsy, the number of cell free DNA molecules obtained from a sample for a given region of the genome and present per reaction after library preparation is low (for example, between 1000 and 16000 NAOIs). Natural breakpoints can be used as molecular identifiers (DePristo et al., 2011, Nature Genetics, 43:491-498). However, the complexity provided by the natural breakpoints is not sufficient to reliably distinguish between all of the starting molecules. The present invention addresses this problem by differentially labelling the NAOIs using oligonucleotides of varying lengths to introduce new, artificial, start and stop read coordinates (or new, artificial, breakpoints) into the NAOIs and thus introduce sufficient variability.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms may be defined below for the sake of clarity and ease of reference.

A first aspect of the invention provides a method of differentially labelling a nucleic acid of interest (NAOI). The method comprises contacting a sample comprising the nucleic acid of interest with a pool of oligonucleotides. The pool comprises oligonucleotides having at least 5 different lengths, and an oligonucleotide from the pool is attached on to one or each end of the nucleic acid of interest, for example by ligation. Random attachment of oligonucleotides to the NAOIs provides variation in the length of oligos attached to the NAOIs in the sample. Attachment of an oligonucleotide moves the read start or stop coordinate when the labelled NAOI is sequenced in a subsequent sequencing step. Specifically, in embodiments of the invention comprising sequencing of the labelled NAOI, the new start and/or stop coordinates (i.e. start and end of the sequence reads) can be used to identifying and distinguish between different starting molecules.

In a more specific method of the invention, the method comprises (a) providing a sample comprising a plurality of NAOIs. Each of the NAOIs had a start coordinate defined by one end of the NAOI and a stop coordinate defined by the other end of the NAOI. A start coordinate is the first nucleotide in a sequencing read when the NAOI is sequenced. A stop coordinate is the last nucleotide in a sequencing read when the NAOI is sequenced. They are referred to as "natural" start and stop coordinates since they are the start and stop coordinate determined by the natural break points in the NAOI. They may also be referred to as the initial start and stop coordinates, or the start and end break points of the NAOI.

The skilled person will appreciate that, depending on the length of the NAOI (for example 150 nucleotides) and the number of sequencing cycles in the subsequent sequencing step of the method (for example 100 cycles to read 100 bases), each NAOI may give rise to a pair of sequencing reads from complementary strands that must be combined to provide the sequence of the NAOI. This is referred to as paired-end sequencing, and is well known in the art. In such embodiments, the natural start coordinate of one read and the natural start coordinate of its paired read in the complementary strand (both at their respective 5' ends) correspond to the natural start and stop coordinates (i.e. breakpoints) of the NAOI. Such situations can be taken into account bioinformatically to provide sequences of the original starting molecules.

The method of labelling NAOIs of interest further comprises a step of (b) contacting the sample with a pool of oligonucleotides, the pool comprising oligonucleotides having at least 5 different lengths.

Each oligonucleotide in the pool comprises a spacer region. Variability in the length of the spacer region can provide the variability in total oligonucleotide length. In some embodiments, the pool of oligonucleotides comprises a mixture of oligonucleotides having at least 5, 6, 7, 8, 9, 10, 11, 12, 13, 14, 15, 20, 25, or at least 50 different lengths of spacer region. A pool comprising at least 20 different lengths of spacer region may be preferred.

In one embodiment of the invention, the pool of oligonucleotides comprises a mixture of oligonucleotides having spacer regions of from 1 to 75 nucleotides, or from 1 to 40, or from 1 to 25 nucleotides in length. Of course, there may be some oligonucleotides in the pool that do not have a spacer region (i.e. the spacer region is 0 nucleotides), although these will always be used in combination with oligonucleotides that do have a spacer region to enable variable length oligonucleotides to be attached to the NAOIs in a random manner.

Larger or smaller pools of oligonucleotides can be used according to the level of complexity needed to identify different starting NAOI molecules. For example, if there are oligonucleotides in the pool having 40 different lengths, assuming an oligonucleotide is attached to both ends of a NAOI, this provides 1600 different possible combinations. Assuming, for example, 400 different natural start/stop co-ordinate combinations (a conservative estimate), this gives a final complexity of 640,000.

The method of labelling NAOIs of interest further comprises a step of (c) attaching an oligonucleotide from the pool to one or each end of a plurality of NAOIs to provide a plurality of labelled NAOIs. Importantly, attachment of the oligonucleotides to the plurality of NAOIs alters the number of base pairs of the NAOI that are obtained when the labelled NAOI is subsequently sequenced.

For example, when a labelled NAOI is sequenced using a next generation sequencing platform, each sequencing round provides the identity of a single nucleotide. For a fixed-length sequence read of, for example, 100 nucleic acids, the number of those nucleotides that correspond to nucleotides in the starting NAOI will change when different length oligonucleotides are attached. If an oligonucleotide is attached that shifts the start coordinate by 25 nucleotides, then only 75 nucleotides of the NAOI will have been obtained (or, in other words, only 75 of the nucleotides in the sequence read will be derived from the NAOI). In this way, although there may be several NAOIs in the pool that have the same sequence due to the natural breakpoints in the nucleic acid, they can be distinguished from one another by taking into account the different length oligonucleotides that are attached. The attachment of oligonucleotides therefore introduces synthetic start and/or stop coordinates. A synthetic start coordinate is the start of the sequence read in a subsequent sequencing step determined by the length of oligonucleotide attached to one end of the NAOI. A synthetic stop coordinate is the end of the sequence read in a subsequent sequencing step as determined by the length of oligonucleotide attached at the other end of the NAOI.

Crucially, this allows the skilled person to identify true mutations in the NAOI and to distinguish them from errors introduced during sequencing and/or processing of the NAOI, since the sequence reads can be grouped according to the underlying sequence of the NAOI and a consensus sequence determined. If a mutation is still present in the consensus sequence, then the skilled person can call the presence of a mutation in the underlying NAOI with more certainty compared to when the underlying NAOI molecules having the same sequence cannot be distinguished from one another.

The oligonucleotides are attached to the NAOIs at either or preferably both ends. Attachment may be achieved by any suitable method, for example ligation, PCR, polymerase extension, isothermal/rolling circle amplification, loop-mediated isothermal amplification, or strand-displacement amplification. Ligation of the oligonucleotides may be preferred. In one embodiment, the method may comprise contacting the sample comprising a plurality of nucleic acids of interest with the pool of oligonucleotides, and further wherein oligonucleotides having spacer regions of at least 2 or at least 3 or at least 4 or at least 5 different lengths are attached to the nucleic acids of interest.

At any suitable stage of the method of the invention, the method may comprise a step of purification, for example to remove un-ligated oligonucleotides. A step of purification may take place after attachment of the oligonucleotides to one or both ends of the NAOIs.

The oligonucleotides are of a design to allow the skilled person to differentiate between the nucleotides in a sequence read arising from the NAOI and the adjacent nucleotides in the sequence read arising from the attached oligonucleotide. For example, the longest spacer region in a pool of oligonucleotides may be a reference sequence whose sequence is known. Therefore, the sequence of the attached oligonucleotide can be distinguished from the sequence of the NAOI. All of the spacer regions align (or overlap) to the same part of the reference sequence, differing only in the total length of the spacer region. Accordingly, in one embodiment, each spacer region in a given pool share 100% identity across their length.

In one embodiment of the invention, the spacer regions of all the oligonucleotides in a given pool may be fragments of the same reference sequence. For example, the spacer regions may consist of a sequence according to $X_1X_n$, wherein:

a) X is any nucleotide;
b) n is 0 to 75 (or 0 to 50, or 0 to 39, or 0 to 24);
c) the sequence of the longest spacer region in the pool is a reference sequence;
d) each spacer region is a fragment of the reference sequence in the pool; and
e) $X_1$ is the first nucleotide in each spacer region.

Note that the sequence of the spacer region may be present according to the above formula ($X_1X_n$) in either the 5' to 3' or 3' to 5' direction.

In such embodiments, each of the spacer regions in the pool of oligonucleotides align at one end. Hence $X_1$ is the same nucleotide and is at the same position in each spacer region (relative to all other spacer regions when they are aligned). For example, a simple pool of spacer regions may be represented by:

```
A

ATC

ATCGA

ATCGATTG
``` wherein the pool comprises oligonucleotides having 4 different spacer region lengths, the sequence ATCGATTG is the reference sequence, $X_1$ is the first A nucleotide in each spacer region, and n is 0 to 7.

In some embodiments, the longest spacer region may be less than or equal to 51 nucleotides in length. In another embodiment, the longest spacer region may be less than or equal to 40 nucleotides in length. In a preferred embodiment, the longest spacer region may be less than or equal to 25 nucleotides in length.

It may be beneficial to have the different lengths of oligonucleotide present in similar quantities or concentrations in a given pool, to prevent a bias towards a particular length of oligonucleotide from being attached to the NAOIs. However, when designing the oligonucleotide pool, the skilled person may make adjustments to the relative frequency or concentration of different lengths of oligonucleotide in the pool to take in account differences in efficiency of attachment of the oligonucleotides to the NAOI. For example, very short sequences may attach more efficiently than longer sequences. However, in order to reduce length bias, in one embodiment of the invention, the oligonucleotides having different lengths are present in the pool in an equimolar, or substantially equimolar, ratio. For example, there may be no length of oligonucleotide that is present at more than 50% frequency than any other length of oligonucleotide. In one embodiment, the frequency (i.e. total number) of each length of oligonucleotide in the pool does not differ between any two different lengths of oligonucleotide by more than 50%.

For further complexity, the NAOIs may be contacted by more than one pool of oligonucleotides. Although the reference sequence (i.e. the sequence of the longest spacer region in a given pool) may differ between pools, the other components (for example the sequence of the filler region) may be the same or they may be different. Accordingly, in one embodiment of the invention, the method comprises contacting the sample comprising the NAOI with a plurality of pools of oligonucleotides, wherein the longest spacer region of each pool is a known reference sequence and further wherein the reference spacer region differs between pools. In one embodiment each oligonucleotide comprises a filler region wherein the filler regions in a given pool of oligonucleotides are the same but the filler regions differ between pools. Alternatively, the filler regions (and other components of the oligonucleotide, apart from the spacer region) may be same even across different pools.

When using multiple pools of oligonucleotides, the NAOIs will be generally contacted by the multiple pools prior to amplification.

In a given pool of oligonucleotides, the complete sequence of each oligonucleotide may be the same across oligonucleotides having the same length. For example, all oligonucleotides that are 50 nucleotides long have the same sequence, all oligonucleotides that are 55 nucleotides long have the same sequence, all oligonucleotides that are 60 nucleotides long have the same sequence etc. However, oligonucleotides of different lengths vary sufficiently to allow any one oligonucleotide to be distinguishable from another length oligonucleotide. Much of the heterogeneity may arise due to differences in the sequence of the spacer region, and so when using multiple pools of oligonucleotides, the oligonucleotides may vary in sequence by more than one nucleotide and the shortest spacer region may be of sufficient length to enable oligonucleotides belonging to different pools to be distinguished from each other, even if they are the same length.

In an oligonucleotide pool, each length of oligonucleotide is distinguishable from every other length of oligonucleotide in the pool by virtue of the length of the spacer region sequence. As a result, it is not necessary for all oligos in the pool to have different sequences (as is required in traditional molecular barcoding techniques known in the art). Instead, all oligonucleotides in a given pool that have the same overall length share the same spacer region sequence. For example, all oligonucleotides in a pool that have a spacer region length of 5 nucleotides share identical spacer region sequences, all oligonucleotides in a pool that have a spacer region length of 6 nucleotides share identical spacer region sequences, all oligonucleotides in a pool that have a spacer region length of 7 nucleotides share identical spacer region sequences etc. In addition, the sequence of each oligonucleotide sequence in the pool is known (to allow the nucleotides in a sequence read arising from an attached oligonucleotide to be distinguished from nucleotides in a sequence read arising from the NAOI to which the oligonucleotide was attached), even though the sequence of the spacer region various between different oligonucleotide lengths. This may be achieved by each oligonucleotide in the pool being a fragment of a known reference sequence, as described above. Alternatively, the sequence of each different fixed length of spacer sequence may be unique to allow them to be distinguished from one another. The precise sequence of the spacer region is not important; provided different lengths of oligos are used and attached to the NAOIs in a random manner, the skilled person can distinguish between different starting molecules by simply counting the number of NAOI-derived nucleotides in the resulting sequence read. It is not necessary to "read" the spacer-region derived (or oligonucleotide-derived) sequence in the sequence read to identify individual starting molecules, since they are distinguishable from each other according to the shifted start and/or stop read coordinates. This is a significant difference from molecular barcoding techniques of the prior art, which require starting molecules to be uniquely labelled using a large pool of different molecular barcode tags, and then starting molecules to be identified using the sequence of the barcode (i.e. the actual identity of the nucleotide bases in the barcode). The sequences of the barcodes in the sequence reads are compared to distinguish between different starting molecules. In contrast, in the present invention, the sequence of the oligonucleotide or spacer region is irrelevant. The length of the oligonucleotide (as determined by the variable spacer region) instead changes the number of NAOI-derived nucleotides in the sequence read and thus uniquely identifies starting molecules.

Further complexity and sensitivity can be achieved by carrying out the method in replicate. For example, in one embodiment the method comprises performing replicate amplification reactions of the labelled NAOI. Different sample indexes may be used for each replicate amplification reaction to enable them to be distinguished from one another. The method comprises sequencing the labelled NAOI in the replicate reactions. In some embodiments, the method comprises splitting the sample into at least 2 (or at least 3 or at least 4) different replicate reactions. Splitting the sample may occur before oligonucleotide attachment and amplification, between oligonucleotide attachment and amplification, or after both oligonucleotide attachment and amplification. An index sequence may also be used when sample replicates are used to identify which replicate the sequence originates from.

The oligonucleotides in the oligonucleotide pool will generally have additional features beyond the simple spacer region.

Each oligonucleotide may comprise a primer binding site, such as a universal priming site, or may incorporate universal priming sites into the NAOIs. When the oligonucleotides in the pool are double stranded, each strand of each oligonucleotide may comprise a primer binding site, such as a universal priming site, or may incorporate universal priming sites into the both strand of the NAOIs. The primer binding sites may be used to amplify the labelled NAOI, for example by using PCR. In embodiments where the oligonucleotide comprises a primer binding sites, the oligonucleotide may comprise an N nucleotide (A, T, G or C, or other non-universal base) immediately adjacent to the UPS.

This N nucleotide acts to interrupt long stretches of complementarity in DNA molecules that have the same or similar variable length oligonucleotides ligated to each end, since long stretches of uninterrupted complementarity can result in DNA secondary structure formation and in complications during sequencing. The N nucleotide may differ between oligonucleotides in the same pool.

In one embodiment, each oligonucleotide also comprise or act as a sequencing adaptor. Sequencing adaptors allow the sequence of a NAOI to be determined using a next-generation sequencing platform. In some embodiments of the invention, the oligonucleotides are asymmetric sequence adaptors (also referred to in the art as Y-stem adaptors). Asymmetric adaptors are double-stranded adaptors having a complementary section and a non-complementary section (where complementary strands are symmetric, and non-complementary strands are asymmetric). The complementary section is a section where the two sequences are complementary and hybridised together. The complementary section is where the spacer region (and possibly other components of the oligonucleotide) are located. The non-complementary section of the asymmetric adaptor acts as the label for the two strands of the NAOI. The different sequences of the two strands in the non-complementary section of the asymmetric adaptor allow the incorporation of a different label on each of the two strands of the labelled NAOI. Suitable Y-stem adaptors include P7/P5 adaptors (Illumina), although the present invention is not limited to the use of these specific adaptors. Preferably, asymmetric labelling of a NAOI in the sample occurs at each end of the NAOI molecule. Asymmetric adaptors may act as sequencing adaptors. In some embodiments the asymmetric adaptors comprise primer binding sites, or may incorporate primer binding sites into the labelled NAOI, that are used in a subsequent PCR amplification reaction.

After the NAOIs have been labelled (using oligonucleotides from the pool), the NAOIs may be amplified, for example using PCR, to enable further processing and analysis. Therefore, the oligonucleotides may additionally enable a PCR reaction to take place, for example by providing a site complementary to primers used in the PCR reaction.

The NAOI may be processed in other ways prior to attachment of the oligonucleotide. For example, the NAOI may have undergone fragmentation and/or end repair. In some embodiments of the invention, the methods may include a step of fragmenting the NAOI and/or end repair of the NAOI. The NAOI may also be phosphorylated at the 5' end(s) and/or have an A-tail added at the 3' end(s). In some embodiments, depending on the method used, the step of end-repairing the NAOI may also provide a suitable A-tail (for example when using a polymerase to end-repair the NAOI). Other processing steps include amplification of the NAOI, for example using whole genome amplification, to increase the overall amount of the NAOI in the reaction before attaching the oligonucleotides.

The oligonucleotides in the pool may be single stranded, although preferably they are double stranded. Accordingly, in one embodiment, the oligonucleotides in the pool are double stranded and the spacer regions in each strand are complementary to one another. When the oligonucleotides in the pool are double stranded, for a given oligonucleotide, the spacer region is generally the same length in both strands and the spacer regions are complementary to one another. Of course, it can be seen that the reference spacer region (the longest spacer region in a given pool of oligonucleotides) is therefore represented by a first sequence and a second, complementary, sequence. When analysing sequence reads obtained by the method, the presence of the complementary reference sequence can be resolved bioinformatically using methods known to the skilled person.

The oligonucleotide may also comprise a filler region. The filler region may be adjacent to the spacer region, and be a stretch of nucleotides between 1 and 20 nucleotides in length. In some embodiments, the filler region is a stretch of nucleotides from 1 to 20, or from 1 to 15, or from 1 to 10 or from 1 to 5 nucleotides in length.

For a given pool of oligonucleotides, the filler region is the same in each of the oligonucleotides in the pool. However, when the oligonucleotides are double stranded, the filler region may be the same in each of the oligonucleotides in the pool with the exception of the filler region of one strand in each oligonucleotide in the pool being one nucleotide longer. In other words, the filler region may comprise an overhang. The overhang may act as a ligation moiety to allow attachment of the oligonucleotides to the NAOIs.

Therefore, the oligonucleotide may comprise a ligation moiety. "Ligation moiety" refers to any nucleotide sequence capable of ligation. Exemplary ligation moieties include overhangs and blunt ends. Overhangs may be an overhang of one or more bases. Single base overhangs may be preferred (for example a single T base overhang). The overhangs can be universal or non-universal bases. The overhang is preferably a non-universal base overhang. Ligation moiety may also refer to a 5' phosphate group.

Accordingly, each oligonucleotide in the pool may comprise, in order, a primer binding site, a spacer region, a filler region, and a ligation moiety. The filler region may also act as a ligation moiety (for example when the filler region comprises an overhang). When the oligonucleotide is a double stranded oligonucleotide, the first strand may comprise, in a 5' to 3' order, a primer binding site, a spacer region, a filler region, and a ligation moiety, and the second (complementary) strand may comprise in a 3' to 5' order, a primer binding site, a spacer region, a filler region, and a ligation moiety. The oligonucleotide may further comprise a non-complementary region, in the case of asymmetric adaptors/oligonucleotides. The non-complementary region allows differential labelling of the two strands of the oligonucleotide (and hence of the two strands of the NAOI to which the oligonucleotide is attached).

Usually, the oligonucleotide will comprise or consist of non-universal bases A, C, T and/or G (with U replacing T when the oligonucleotide is an RNA oligonucleotide). "Non-universal nucleotide base" and "non-universal base" refer to nucleotide bases that only pair with one type of base under stringent conditions, or has a strong preference for only one type of base. Non-universal bases include the standard "natural" bases A, T, C, G and U. The IUPAC system of nomenclature is used herein, nucleobases are represented by the first letters of their chemical names: A (Adenine), T (Thymine), C (Cytosine), G (Guanine) and U (Uracil). Other non-universal bases beyond the standard bases that may be included in the oligonucleotide include unnatural base pairs (UBPs) such as 5-methylcytosine, 5-hydroxymethylcytosine, hypoxanthine, xanthine, 7-methylguanine and 5,6-dihydrouracil.

However, in some embodiments, the oligonucleotide may comprise one or more universal bases. The oligonucleotide may therefore comprise a mixture of universal and non-universal bases. In the case of double stranded oligonucleotides, either one or both strands of the oligonucleotide may comprise universal bases. In some embodiments, the oligonucleotide (for example a first strand of a double stranded oligonucleotide) may comprise at least 1, 2, 3, 4, 5, 6, 7, 8, 9, 10, 11 or at least 12 universal bases. In one embodiment, the oligonucleotide (for example a first strand of a double stranded oligonucleotide) may comprise from 1 to 20 universal bases, or from 2 to 8 universal bases.

"Universal nucleotide base", "universal base" and "degenerate base" refer to bases that are able to hybridise to more than one type of nucleotide under stringent conditions. For example, a universal base may be able to base pair with each or a subset of the natural DNA bases with little or no discrimination between them.

A universal (or degenerate) base pairs indiscriminately in any sequence context, or at least does not have a strong preference for a particular type of base under stringent conditions. Thus unlike the bases A, T, C, G and U, universal bases pair with more than one other type of base under stringent conditions. The universal/degenerate base may be selected from the group consisting of 2'-deoxyinosine (inosine) and derivatives thereof, nitroazole analogues and derivatives thereof, hydrophobic aromatic non-hydrogen-bonding bases and derivatives thereof, 3'-nitropyrrole bases and derivatives thereof (for example 3'-nitropyrrole CE phosphoramidite), nitroindole bases and derivatives thereof (for example 4-, 5- and 6-nitroindole CE phosphoramidite and 5-nitroindole-3-carboxamide), 2'-deoxynucleoside and derivatives thereof, K-2'-deoxyribose (dk), P-2'-deoxyribose (dP), 2'-deoxyisoguanine and 2'-deoxynebularine. In one embodiment, the universal base is selected from the group consisting of K-2'-deoxyribose and P-2'-deoxyribose. The spacer regions may comprise a single type of universal base (such as inosine), or the spacer regions may comprise a mixture of more than one type of universal base. "Type" in this context refers to the specific species of universal base, for example each of 2'-deoxyinosine (inosine), 3'-nitropyrrole CE phosphoramidite, 4-, 5- and 6-nitroindole CE phosphoramidite and 2'-deoxynucleoside are all different types (or "species") of universal base.

Universal base analogues with no pairing bias and no alteration in stability are reviewed in Loakes D. (2001) Survey and summary: The applications of universal DNA base analogues. Nucleic Acids Res, 29 (12): 2437-2447, the contents of which are incorporated by reference herein. The degenerate bases dP and dk are further described in P. Kong Thoo Lin. and D. M. Brown, Nucleic Acids Res., 1989, 17, 10373-10383 and P. Kong Thoo Lin. and D. M. Brown, Nucleic Acids Res., 1992, 20, 5149-5152, the contents of which are incorporated by reference herein.

When universal bases such as nitroindole and 5-nitroindole-3-carboxamide are used, it may be necessary to use existing and new bespoke polymerases that are able to incorporate dNTPs and extend across such types of universal base (as discussed in, for example, Loakes, et al (2009) J Am Chem Soc. 131 (41) Evolving a polymerase for hydrophobic base analogues, the contents of which are incorporated by reference herein). When using universal bases such as K-2'-deoxyribose and P-2'-deoxyribose, it may be necessary to use polymerases that have an inactivated uracil binding pocket in order to allow strand extension across such universal bases (e.g. KAPA HiFi HotStart Uracil+ReadyMix, VeraSeq Ultra, Phusion U Hotstart DNA Polymerase); or polymerases that lack proof reading activity such as taq.

The presence of the one or more universal bases in the oligonucleotide provides a PCR cycle generator sequence or region, since each round of PCR amplification has the capacity to generate a new PCR cycle counter sequence in the daughter molecules. The total number of sequence reads for a given PCR cycle counter can therefore be used as an indicator of the point at which this sequence was generated from the parental strand, since a PCR cycle counter sequence generated earlier in the PCR amplification will have a larger number of copies than a PCR cycle counter sequence generated later in the PCR amplification. The PCR cycle counter also provides additional opportunities for error correction of the nucleic acid sequence reads, as discussed further below. The PCR cycle counter can alternatively be referred to as a "PCR cycle identifier", since it allows a skilled person to differentiate between amplicons generated in different PCR cycles, or a PCR cycle tracer or PCR cycle tracker.

The universal bases, if present, may be distributed in a contiguous or non-contiguous arrangement throughout the oligonucleotide. When present as a contiguous stretch of universal bases, the universal bases can be 5' or 3' of the spacer region.

In one embodiment, the universal bases may be present within the spacer region. When universal bases are included in the spacer region, the spacer region may be from 5 to 75 nucleotides, or from 8 to 75 nucleotides, or from 8 to 40, or from 8 to 25 nucleotides. For example, in a given pool of oligonucleotides, each spacer region may be from 8 to 40 nucleotides in length and comprise at least one universal base (for example 8 to 40 nucleotides in length with up to 8 universal bases).

In another embodiment, the oligonucleotide comprises a separate PCR cycle counter generator region. The PCR cycle counter generator region may comprise universal and non-universal bases. For example, the PCR cycle counter generator region may comprise at least one universal base and at least one non-universal base. In one embodiment of the invention, the PCR cycle counter generator region comprises from 1 to 20 nucleotides including at least 2 universal bases.

Further possible components of the oligonucleotides include an index sequence. Alternatively, index sequences may be separately attached to the NAOI. The index sequence can be used to identify the sample in subsequent sequencing and analysis.

In one embodiment of the invention, the oligonucleotide is double-stranded and comprises two strands. The first strand comprises a variable length spacer region and a PCR cycle counter generator region comprising one or more universal nucleotide bases and has a ligation moiety at its 3' end. The second strand comprises a complementary variable length spacer region and a sequence complementary to the PCR cycle counter generator region, and a ligation moiety at its 5' end. The two strands hybridise together under stringent conditions.

The oligonucleotides may be DNA or RNA oligonucleotides, but are preferably DNA oligonucleotides.

In one embodiment of the invention, the oligonucleotide comprises a sequencing adaptor, a variable length spacer sequence, and a filler region. In one embodiment of the invention, the oligonucleotide comprises a sequencing adaptor, a variable length spacer sequence, a PCR cycle counter generator region and a filler region.

In one embodiment of the invention, the oligonucleotide comprises ligation moieties at one end (i.e. a ligation moiety at the 5' end of one strand and a ligation moiety at the 3' end of the other strand). The ligation moieties are at the opposite end to the sequence adaptors, if present.

In one embodiment of the invention, the oligonucleotide does not comprise any ligation blocks. "Ligation block" refers to any sequence or moiety that prevents ligation of the nucleic acid to another nucleic acid or nucleotide base. Any suitable ligation block can be used, for example a non-phosphorylated nucleotide, an inverted dT, a C3 spacer, or a 3' phosphate group. A non-phosphorylated nucleotide is preferred.

In one embodiment of the invention, the oligonucleotide comprises a first strand comprising, in a 5' to 3' order, a sequencing adaptor, a variable length spacer sequence, a filler region, and a ligation moiety, and a second strand comprising, in a 3' to 5' order, a sequencing adaptor, a complementary variable length spacer sequence, a complementary filler region, and a ligation moiety. The oligonucleotide may further comprise a PCR cycle generator region in the first strand and a region complementary to the PCR cycle generator in the second strand. The PCR cycle generator region, if present, can be positioned at any suitable position of the oligonucleotide. For example, the PCR cycle generator region may be position between the variable length spacer region and the filler region.

In one embodiment of the invention, the oligonucleotide comprises a first strand comprising, in a 5' to 3' order, a sequencing adaptor, a variable length spacer sequence, a filler region, and a ligation moiety, and a second strand comprising, in a 3' to 5' order, a sequencing adaptor, a complementary variable length spacer sequence, a complementary filler region, and a ligation moiety. The oligonucleotide may further comprise a PCR cycle generator region in the first strand and a region complementary to the PCR cycle generator in the second strand.

The sequencing adaptors may be an asymmetric sequencing adaptors (having a complementary section and a non-complementary section). The sequencing adaptor may be partial sequencing adaptors. The sequencing adaptors may incorporate universal priming sites and/or sequencing primer sites into the NAOI. The sequencing adaptor may be partial Illumina adapter sequences, whereby one strand contains the partial P5 illumina adapter sequence and the complementary strand contains a partial P7 illumina adapter sequence.

In embodiments in which the oligonucleotide comprises a PCR cycle counter generator region, a mixture or pool of PCR cycle counter generator regions may be used that increase the variety of resulting PCR cycle counter sequences that may be generated. A mixture of two or more types of PCR cycle counter generator regions (of different sequence) may be used to increase the diversity of PCR cycle counter sequences that are generated. The PCR cycle counter generator regions differ in their sequence, for example such that the positions of the one or more universal bases are not identical in all PCR cycle counter generator regions in the pool of oligos, or alternatively the "constant" part of the PCR cycle counter generator regions (consisting of non-universal bases) may differ between PCR cycle counter generator regions to cause the relative positions of the universal bases to shift (hence providing more than one "type", i.e. sequence, of oligonucleotide). In such mixtures, the PCR cycle counter generator regions may have two or more arrangements of universal and non-universal bases (i.e. sequences). The mixtures may comprise more than 2 different types of PCR cycle counter generator regions. For example, the mixture may comprise at least 2, at least 3, at least 4, at least 5, at least 6, at least 7, at least, 8, at least 9, or at least 10 different oligonucleotides. A mixture of at least 4 different PCR cycle counter generator regions may be preferred. In such mixtures, it may be preferred that each PCR cycle counter generator regions has at least 4 universal bases, where the arrangement (i.e., position) of universal and non-universal bases in each type of PCR cycle counter generator regions in the mixture is different, and/or wherein the arrangement of non-universal bases differs to cause a shift in the relative locations of the universal bases. The precise design of the PCR cycle counter generator regions is not fixed and the skilled person would understand how to create a mixture of different types of PCR cycle counter generator regions that can provide a sufficient number of different PCR cycle counter sequences, as required by the context. The number of possible PCR cycle counter sequences that can be generated using the oligonucleotides or mixtures of the invention can be at least 2, at least 3 or at least. Preferably, the oligonucleotide or mixture of oligonucleotides is capable of producing at least 4 different PCR cycle counter sequences.

In one embodiment of the invention, the oligonucleotide comprises a first strand comprising, a 5' sequencing adaptor, a variable length spacer sequence, a PCR cycle counter generator region, and a 3' ligation moiety, and a second strand comprising a 3' sequencing adaptor, a complementary variable length spacer sequence, a region complementary to the PCR cycle counter generator, and a 5' ligation moiety. The oligonucleotide may further comprise a filler region.

The order of the components is not absolutely fixed, but the following double-stranded oligonucleotides having a first and second strand may be used in the methods of the invention:

a) a first strand comprising, in a 5' to 3' order, a sequencing adaptor, a variable length spacer region, and a ligation moiety, and a second strand comprising, in a 3' to 5' order, a sequencing adaptor, a complementary a variable length spacer region, and a ligation moiety;

b) a first strand comprising, in a 5' to 3' order, a sequencing adaptor, a PCR cycle counter generator region, a variable length spacer region, and a ligation moiety, and a second strand comprising, in a 3' to 5' order, a sequencing adaptor, a region complementary to the PCR cycle counter generator, a complementary a variable length spacer region, and a ligation moiety;

c) a first strand comprising, in a 5' to 3' order, a sequencing adaptor, a variable length spacer region, a PCR cycle counter generator region, and a ligation moiety, and a second strand comprising, in a 3' to 5' order, a sequencing adaptor, a complementary variable length spacer region, a region complementary to the PCR cycle counter generator, and a ligation moiety;

d) a first strand comprising, in a 5' to 3' order, a sequencing adaptor, a PCR cycle counter generator region, a variable length spacer region, a filler region, and a ligation moiety, and a second strand comprising, in a 3' to 5' order, a sequencing adaptor, a region complementary to the PCR cycle counter generator, a complementary variable length spacer region, a complementary filler region, and a ligation moiety;

e) a first strand comprising, in a 5' to 3' order, a sequencing adaptor, a variable length spacer region, a PCR cycle counter generator region, a filler region, and a ligation moiety, and a second strand comprising, in a 3' to 5' order, a sequencing adaptor, a complementary variable length spacer region, a region complementary to the PCR cycle counter generator, a complementary filler region, and a ligation moiety;

f) a first strand comprising, in a 5' to 3' order, a sequencing adaptor, a first primer binding site, a PCR cycle counter generator region, a variable length spacer region, and a ligation moiety, and a second strand comprising, in a 3' to 5' order, a sequencing adaptor, a second primer binding site complementary to the first primer binding site, a region complementary to the PCR cycle counter generator, a complementary variable length spacer region, and a ligation moiety;

g) a first strand comprising, in a 5' to 3' order, a sequencing adaptor, a first primer binding site, a variable length spacer sequence, a PCR cycle counter generator region, and a ligation moiety, and a second strand comprising, in a 3' to 5' order, a sequencing adaptor, a second primer binding site complementary to the first primer binding site, a complementary variable length spacer region, a region complementary to the PCR cycle counter generator, and a ligation moiety;

h) a first strand comprising, in a 5' to 3' order, a sequencing adaptor, a first primer binding site, a PCR cycle counter generator region, a variable length spacer region, a filler region and a ligation moiety, and a second strand comprising, in a 3' to 5' order, a sequencing adaptor, a second primer binding site complementary to the first primer binding site, a region complementary to the PCR cycle counter generator, a complementary variable length spacer region, a complementary filler region, and a ligation moiety; or i) a first strand comprising, in a 5' to 3' order, a sequencing adaptor, a first primer binding site, a variable length spacer region, a PCR cycle counter generator region, a filler region and a ligation moiety, and a second strand comprising, in a 3' to 5' order, a sequencing adaptor, a second primer binding site complementary to the first primer binding site, a complementary variable length spacer region, a region complementary to the PCR cycle counter generator, a complementary filler region, and a ligation moiety;

Note the first and second primer sites are generally complementary to each other. In addition, the first and second primer binding sites may be contained within the sequencing adaptors. Such sequencing adaptors would generally comprise an asymmetric portion, and a complementary portion. The first and second primer binding sites may be contained within the complementary portion containing, or the first and second primer binding sites may span the complementary and non-complementary sections. The primer sites may be used in the subsequent PCR reaction and/or sequencing steps. The benefit of including the sequencing adaptors in the oligos is that it avoids the need for a further ligation step to attach the sequencing adaptors to the NAOIs.

The PCR cycle counter generator region may comprise up to 20 nucleotides, including at least 2 universal bases. The variable length spacer sequence may comprise up to 75 non-universal nucleotides. The filler region may comprise up to 20 non-universal nucleotides.

In addition to the above arrangements, in particular when the oligo does not already contain asymmetrical sequencing adaptors, the oligo may further comprise a ligation moiety at the 5' end of one strand (i.e. the strand that already comprises a ligation moiety at the 3' end). In any of the above arrangements, the oligo may further comprise a ligation block at the 3' end of the complementary strand to prevent blunt-ended ligation to a second adapter (adapter dimerization).

The method of labelling NAOIs further comprises a step of (d) amplifying the labelled NAOIs. In particular, once the NAOIs are labelled, they are amplified to increase the total number of nucleic acids to allow them to be further processed. Indeed, the methods of the invention may comprise a number of amplification reactions. For example, and most commonly, amplification of the NAOIs may be carried out after the NAOIs are labelled. In addition, amplification may be carried out prior to labelling to increase the amount of starting molecules.

In some embodiments, the methods of the invention may comprise a step of target enrichment. The target enrichment step, if present, is generally conducted after the NAOI is labelled, and preferably after the labelled NAOI has been amplified. Target enrichment can be carried out according to any method known to the skilled person, for example as discussed in Mamanova et al., "Target-enrichment strategies for next-generation sequencing", 2010, Nature Methods, 7:111-118, Bodi et al., "Comparison of Commercially Available Target Enrichment Methods for Next-Generation Sequencing", 2013, J Biomol Tech., 24 (2): 73-86, or Gnirke et al., "Solution Hybrid Selection with Ultra-long Oligonucleotides for Massively Parallel Targeted Sequencing", 2009, 27 (2): 182-189, all of which are incorporated herein by reference. Target enrichment allows the subsequent sequencing and analysis steps to focus on a genetic region of interest. Methods of target enrichment include RNA probe enrichment (for example Agilent™ SureSelect™ target enrichment), DNA probe enrichment (for example NimbleGen™ SeqCap EZ Choice™ enrichment) or array-based enrichment (for example NimbleGen™ array capture enrichment). If target enrichment is conducted, a subsequent amplification may also be employed in the method. Clonal amplification can be undertaken as part of the step of determining the sequence of the NAOI.

The method of labelling NAOIs of interest further comprises a step of (e) sequencing the labelled NAOIs to provide a library of sequence reads. Determining the sequence of labelled, amplified and optionally enriched NAOI can be carried out according to any suitable method known to the skilled person. However, given the number of NAOIs that will be analysed in any given method, next-generation sequencing (NGS) methods are preferred. Next-generation sequencing is also referred to as high-throughput sequencing and massively-parallel sequencing in the art, and is known and understood by the skilled person. A review of next-generation sequencing techniques is provided in Goodwin et al., "Coming of age: ten years of next-generation sequence technologies", 2016, Nature Reviews, 17:333-351, the contents of which are incorporated by reference herein.

Each sequence read will generally comprise am oligonucleotide-derived portion and a NAOI-derived portion. For a given number of sequencing cycles, the length of the NAOI-derived portion will be influenced by the length of oligonucleotide that was attached to the NAOI.

The next-generation sequencing employed by the present invention may be selected from the group consisting of sequence-by-synthesis (SBS), sequencing-by-ligation (SBL) and long-read sequencing (LRS). The sequencing-by-synthesis may be selected from the group consisting of cyclic reversible termination SBS and single-nucleotide addition SBS. The long-read sequencing may be selected from the group consisting of single-molecule LRS and synthetic long-read LRS. Methods of sequence determination using sequencing-by-synthesis may be preferred.

The method of labelling NAOIs further comprises a step of (f) grouping the reads according to the sequence obtained (i.e. derived or arising) from the NAOI. This is a bioinformatic step that will be carried out by a computer. Each sequence read will comprise a NAOI-originating portion and a spacer region-originating portion. The sequence reads may comprise further components, such as filler region-originating portion, a PCR cycle counter sequence, and/or a molecular barcode-originating portion, depending on what features were incorporated into the adaptors or into the NAOIs during the method.

In such a step, the reads are aligned according to the part of their sequence that represents the NAOI sequence (i.e. the NAOI-derived portion of the sequence reads are aligned to each other). Since the sequence of the attached oligonucleotides is already known, this is easily achieved, since the NAOI-derived portion of the sequence read can be distinguished from the known oligonucleotide-derived portion of the sequence read.

When step (f) is achieved by grouping the reads according to the sequence obtained from the NAOI, the NAOI-derived section of each sequence read is identical or substantially identical in all of the sequence reads in a given group. This is because each sequence read was (ultimately) generated from the same starting labelled NAOI, prior to its amplification. Although in the starting sample there may be more than one NAOI having the same length and the same sequence, the method of the invention can distinguish between such molecules since random attachment of oligonucleotides of varying lengths to one or both ends of the NAOI will shift the start and/or stop coordinates in the resulting sequence read. Thus, although the NAOI-derived portion of the sequence read may be the same, the length of the NAOI-derived portion will differ depending on the length of the oligos attached to the NAOI.

"Identical" means each NAOI-derived region of the sequence reads in a group have the same sequence (including the same natural start and stop coordinates) and the same length. "Substantially identical" also encompasses NAOI-derived regions of the sequence reads in a given group having at least 95% identity to all other NAOI-derived regions in the same group, to take into account, for example, possible errors introduced during the sequencing or processing of the NAOIs. Percent identity can be determined according to methods known to the skilled person, and most simply can be calculated by dividing the total number of identical nucleotides by the total number of nucleotides in the query sequence.

For the purposes of this grouping step that relies solely on the sequence originating from the underlying NAOI (before attachment of the oligonucleotide), the identity of the base pairs of the sequence of the attached oligonucleotides can be ignored (or the base pairs of the attached oligonucleotide can be removed from the sequence read prior to grouping).

Accordingly, in one embodiment of the invention, grouping the sequence reads according to the sequence of the NAOI comprises grouping all identical or substantially identical NAOI-derived regions of the sequence reads to uniquely identify different starting NAOI molecules. This may comprise removing sequences from the sequence read that are not NAOI-derived regions (for example, regions of the sequence read arising from the spacer sequence, the universal priming site, the filler region, or any other parts of the attached oligonucleotide).

The step of sequencing may provide two sets of sequence reads from each amplified and labelled NAOI, a first set from one end of the NAOI and a second end from the other end of the NAOI. The step of grouping the sequence reads may comprise pairing sequence reads obtained from the same starting labelled NAOI. This is referred to as paired-end sequencing and is known in the art. Paired-end sequencing can be used in combination with the grouping methods disclosed herein to provide complete sequences of the NAOIs (with or without attached oligonucleotides). Accordingly, in some embodiments, the sequencing method used comprises paired-end sequencing.

In one embodiment of the invention grouping the sequence reads according to the sequence of the NAOI comprises grouping the sequence reads according to the natural start and end coordinates to provide groups of paired-end reads and, within each group of paired-end reads, sub-grouping the sequence reads according to the synthetic start and/or stop coordinates to provide sub-groups of paired-end reads. Each sequence read in a given group of paired-end reads has the same natural start and end coordinates. The natural start coordinate is determined by the first base in the NAOI prior to labelling with an oligonucleotide and the natural stop coordinate is determined by the last base in the NAOI prior to labelling with an oligonucleotide. Furthermore, each sequence read in a given sub-group of paired-end reads has the same natural start and end coordinates and the same synthetic start and end coordinates.

Alternatively, this can be done vice versa (grouping the sequence reads according to the synthetic start and end coordinates to provide groups of paired-end reads (wherein each sequence read in a given group of paired-end reads has the same synthetic start and end coordinates) and, within each group of paired-end reads, sub-grouping the sequence reads according to the natural start and/or stop coordinates to provide sub-groups of paired-end reads (wherein each sequence read in a given sub-group of paired-end reads has the same synthetic start and end coordinates and the same natural start and end coordinates)).

The method of labelling NAOIs further comprises a step of (g) determining a consensus sequence for each NAOI. This allows the sequence of the original NAOI to be determined and for errors introduced during processing of the sample to be minimised.

In one embodiment, determining a consensus sequence for each NAOI comprises identifying the most abundant (i.e. modal) nucleotide at each nucleotide position in a given group of reads.

Accordingly, the sequences of the NAOIs can be determined and corrected for errors introduced during the processing and analysis of the molecules.

If universal bases were present in the oligonucleotides, an additional grouping step may be performed to further enhance the sensitivity of the method and to improve the error correction capability.

The presence of universal bases means that each time a cycle of PCR is performed, the starting NAOI molecule to which the oligonucleotide was attached generates a new copy having randomly incorporated bases opposite the universal base in the oligonucleotide. This effectively acts as a "PCR cycle counter", i.e. a record of the number of cycles of PCR, since a new PCR cycle counter is generated each cycle. During amplification, every copy of the original parental strand could generate a different daughter strand since the bases opposite the universal base will be incorporate at random (or semi-randomly). Thus each cycle of PCR effectively generates a tag that identifies a further copy of the original parental strand.

Although the number of universal bases will likely not be sufficiently high to produce a unique sequence for each cycle of PCR, the introduction of even a small number of universal bases in the oligonucleotide can provide very helpful information. For example, even though PCR has an inherent error rate, because the starting molecule will generate a new copy each time, an accurate copy of the NAOI should have highest number of different PCR counters associated with it.

In some embodiments, the methods of the invention comprise counting or quantifying the number of different PCR counter sequences associated with each group of sequence reads. For example, in one embodiment, the method of the invention comprises:

a. either:
  i. grouping the sequence reads according to the natural start and end coordinates to provide groups of paired-end reads; and
  ii. within each group of paired-end reads, sub-grouping the sequence reads according to the synthetic start and/or stop coordinates to provide sub-groups of paired-end reads;
or:
  i. grouping the sequence reads according to the synthetic start and/or stop coordinates to provide groups paired-end reads; and
  ii. within each group of paired-end reads, sub-grouping the sequence reads according to the natural start and end coordinates to provide sub-groups of paired-end reads;
and
b. counting the number of different PCR cycle counter sequence associated with each NAOI sequence in each sub-group; and
c. determining a consensus sequence for the NAOI in each sub-group of paired-end reads. The NAOI sequence having the highest number of different PCR cycle counters associated with it may be considered the true sequence. The consensus sequence may be determined on a nucleotide-by-nucleotide basis. The determination of a consensus sequence may therefore require consideration of the frequency of the identity of each nucleotide in a sequence, and the number of different PCR counter sequences associated with the identity of each nucleotide, rather than just considering each sequence read as a whole The methods of the present invention may comprise the step of grouping the sequence reads to group together all sequence reads having the same PCR counter sequence. The sequence of the PCR counter is determined by the identity of the nucleotides at the positions in the sequence read corresponding to the positions of the universal bases in the oligonucleotide. The PCR counter may therefore be contiguous or non-contiguous, depending on the arrangement of universal bases in the oligonucleotide that was attached to the starting NAOI molecule.

Once the sequence reads have been grouped in this way, sequences or nucleotides that are associated with the largest number of different PCR counter sequences are more likely to be accurate copies of the originating NAOI sequence. Sequences or nucleotides having a smaller number of different PCR counters can be discarded as likely being the result of an error introduced during PCR.

The step of grouping the sequence reads according to the sequence of the PCR counter can be done before or after grouping the sequence reads according to the sequence of the NAOI. For example, the grouping steps could be:
  a) group by NAOI sequence, then by PCR counter sequence;
  b) group by PCR counter sequence, then by NAOI sequence;
  c) group by the natural start and stop coordinates, then by the synthetic start and stop coordinates, and then by PCR counter sequence; or
  d) group by PCR counter sequence, then by the natural start and stop coordinates, and then by the synthetic start and stop coordinates.

A consensus sequence can be defined as a sequence occurring in at least 20%, at least 30%, at least 40%, at least 50%, at least 60%, at least 70%, at least 80% or at least 90% of all sequence reads for a single originating nucleic acid of interest. Preferably the sequence occurs in at least 50% of the sequence reads (although can be lower, for example if the attached oligonucleotide contains a PCR counter). In this way, the method can be used to determine the true sequence of a starting molecule and to reduce or eliminate errors introduced by the method, in particular errors introduced by the polymerase in PCR reactions.

"Consensus sequence" as used herein refers to the sequence of the NAOI that is determined to be most likely sequence of the original NAOI. The nature of the amplification and sequencing steps means errors may be introduced into the resulting sequence read. The present invention allows error correction of the sequence read, and correcting such errors allows the skilled person to arrive at a "consensus sequence" as being the most likely sequence of the original NAOI. For example, the consensus sequence may be determined by the most commonly reported nucleic acid at a given position of the NAOI. Since the invention allows individual starting molecules to be identified and the sequence reads to be grouped accordingly, even low allelic fraction mutations or other changes can be identified. Alternatively, the consensus sequence may be determined by the reported nucleic acid at a given position of the NAOI that is associated with the highest number of different PCR cycle counter sequences. In some embodiments, the consensus sequence may be determined with reference to both the relative frequency of each nucleotide reported at a given position, and the number of different PCR cycle counters associated with nucleotide reported at a given position.

The PCR counter is an indicator of the number of times a given sequence is amplified from an originating nucleic acid of interest. In some embodiments of the invention, the method may comprise determining the number of PCR counters for each group of sequence reads. A consensus sequence may then be obtained by retaining the sequence having the highest number of different PCR counters as a consensus sequence for the originating nucleic acid of interest.

Often, identification of the consensus sequence may be done by reference to a combination of the number of reads and the number of PCR counters. For example, if a consensus sequence cannot be determined solely by the number of reads originating from a parental NAOI, then reference can be made to the number of PCR counters for each read to help reach a decision on the consensus sequence. In one embodiment of the invention, the step of determining a consensus sequence requires determining the frequency with which a given sequence is present in the dataset of sequence reads and determining the number of different PCR counters associated with that sequence. A determination of the consensus sequence can then be made accordingly.

Consensus sequences may be determined on a nucleotide-by-nucleotide basis. The determination of a consensus sequence therefore requires consideration of the frequency of the identity of each nucleotide in a sequence, and the number of different PCR counter sequences associated with the identity of each nucleotide, rather than just considering each sequence read as a whole.

In some embodiments of the invention, distinguishing true variants in parental NAOI sequences from false variants in a parental NAOI sequence comprises counting or quantifying the number of different PCR counter sequences. In particular, the method may comprise counting the number of different PCR cycle counter sequences originating from each parental NAOI or associated with each NAOI sequence in the sequence reads. Due to the nature of the present methods, the larger the number of different PCR counter sequences associated with each different NAOI-originating component or portion thereof, the higher probability there is of the variant being a true variant. The larger the number of different PCR counter sequences associated with each different NAOI-originating portion, the higher the probability the nucleic acid sequence accurately represents the parental NAOI.

In some embodiment, the methods comprise distinguishing sequence reads from each other according to the stage at which the sequence was made during the first PCR amplification reaction.

In some embodiments, the method comprise distinguishing true variants in parental NAOI sequence from false variants in parental NAOI sequence comprising quantifying the relative amount of each different PCR cycle counter for a given NAOI sequence. A gradual (e.g. logarithmic) decrease in the relative amount of each PCR cycle counter for a given NAOI sequence indicates the reads may have originated from the same starting molecule. For a given NAOI sequence, if there are multiple different PCR cycle counter sequences present in the same or similar quantity, they are likely to have originated from different starting molecules. If the same variant occurs in multiple starting molecules, the higher the probability the variant is a true call of the parental NAOI sequence. When conducting PCR, the number of cycles of PCR is known, since the cycles are controlled according to the reaction conditions. Accordingly, in one embodiment of the invention, the step of distinguishing true variants in parental NAOI sequence from false variants in parental NAOI sequence comprises comparing the number of PCR cycle counter sequence associated with each different NAOI-originating portion with the number of PCR cycles performed in the PCR step that generated the PCR cycle counter sequences. When the number of different PCR counter sequences associated with a given NAOI-originating portion is greater than the number of PCR cycles performed, this is indicative of a true variant.

In one embodiment of the invention, the step of distinguishing true variants in a parental NAOI sequence from false variants in a parental NAOI sequence comprises:
a. grouping the sequence reads to group together all sequence reads arising from the same parental NAOI molecule;
b. counting the number of different PCR cycle counters associated each different NAOI-originating component sequences.

The method may additionally comprise a step of mapping the sequence reads to a reference genome or reference sequence (or database of reference sequences). Generally the reference sequences will be from the same species from which the NAOI originated. The step of mapping of the sequence reads to a reference may occur prior to grouping or aligning the sequence reads according to the methodology outline above. In some embodiments, the mapping of the sequence reads to a reference may occur after obtaining a consensus sequence. If target enrichment took place in the method, then the reference sequence will correspond to the target for which the reaction mixture was enriched. This greatly simplifies the analysis that must be undertaken.

To compare the NAOI sequences of the sequenced sample to each other and/or to a reference sequence, the sequences may be aligned (mapped) to each other and/or to a reference sequence; variation within the sequences can then be identified. Reads may be aligned to each other and/or to a reference sequence and analysed using bioinformatics software. Tools for mapping high-throughput sequencing data are reviewed by Fonseca et al., Bioinformatics. 2012 Dec. 15; 28 (24): 3169-77, the contents of which is incorporated herein in its entirety.

After alignment, differences can be identified between the sequences and/or between the sequences and a reference sequence (e.g. a reference genome sequence). To identify variation, sequences may be grouped by sequence similarity; such a comparison allows some mismatches and small structural variation (e.g. InDels) in sequence.

In some embodiment, the method comprises determining the presence or absence of a genetic alteration in the nucleic acid of interest.

The NAOIs may be contained in or derived from a sample from a patient. In some embodiments, the sample is a biological sample obtained from a subject, or a sample containing nucleic acid of interest that is extracted from a biological sample obtained from a subject. The sample can be a tissue sample, for example a surgical sample. Preferably the sample is a liquid biopsy sample, such as blood, plasma, serum, urine, seminal fluid, stool, sputum, pleural fluid, ascetic fluid, synovial fluid, cerebrospinal fluid, lymph, nipple fluid, cyst fluid, or bronchial lavage. In some embodiments the sample is a cytological sample or smear or a fluid containing cellular material, such as cervical smear, nasal brushing, or esophageal sampling by a sponge (cytosponge), endoscopic/gastroscopic/colonoscopic biopsy or brushing, cervical mucus or brushing.

Many of the above samples can be obtained non-invasively, and can therefore be taken regularly without great risk or discomfort to the subject. Methods of the invention may comprise a step of obtaining a sample from a patient. Alternatively, the methods may be carried out on samples previously obtained from a patient (i.e., ex vivo/in vitro methods). In one embodiment of the invention, samples and/or NAOIs of interest are obtained by dialysis.

Samples may be obtained from patients suspected of having a particular disease or condition, such as cancer. Such a disease or condition can be diagnosed, prognosed, monitored and therapy can be determined based on the methods, systems and kits described herein. Samples may be obtained from humans or from animals, such as a domesticated animal, for example a cow, chicken, pig, horse, rabbit, dogs, cat, or goat. Usually, a sample will be derived from a human.

To obtain a blood sample, any technique known in the art may be used, e.g., a syringe or other vacuum suction device. A blood sample can be optionally pre-treated or processed prior to tagging and analysis. Examples of pre-treatment steps include the addition of a reagent such as a stabilizer, a preservative, a fixant, a lysing reagent, a diluent, an anti-apoptotic reagent, an anti-coagulation reagent, an anti-thrombotic reagent, magnetic property regulating reagent, a buffering reagent, an osmolality regulating reagent, a pH regulating reagent, and/or a crosslinking reagent. In addition, plasma may be obtained from the blood sample, and the plasma be used in the subsequent analysis. A blood sample may be processed to remove cells to obtain plasma, for example by centrifugation and/or filtration.

When obtaining a sample from a human or an animal (e.g., blood sample), the amount can vary depending upon human or animal size and the condition being screened. In some embodiments, up to 50, 40, 30, 20, 10, 9, 8, 7, 6, 5, 4, 3, 2, or 1 mL of a sample is obtained. In some embodiments, 1-50, 2-40, 3-30, or 4-20 ml of sample is obtained. In some embodiments, more than 5, 10, 15, 20, 25, 30, 35, 40, 45, 50, 55, 60, 65, 70, 75, 80, 85, 90, 95 or 100 ml of a sample is obtained.

A sample may be processed prior to undergoing further analysis. Such processing steps may comprise purification (for example removal of cells and/or debris from the sample) or extraction or isolation of the NAOI from the sample. In one embodiment, processing of the sample comprises:
  a) purification of the sample to obtain a purified sample comprising the nucleic acid of interest;
  b) extraction or isolation of the nucleic acid of interest from the patient sample; and/or
  c) enrichment of the sample for the NAOI.

Possible methods to purify the sample include centrifugation. Possible extraction methods include, for example, magnetic-bead-based extraction or silica-membrane-based extraction. Purification or extraction methods will also act to enrich the sample for the NAOI, or further, separate, steps may be taken to enrich the sample. The sample may also be processed during the course of the method to remove unwanted components, for example purification of a reaction mixture comprising NAOIs having one or more oligonucleotides attached to remove unligated oligos. Suitable and appropriate methods of purification will be familiar to the skilled person.

The sample might not always be a patient sample, but instead could be a sample obtained from the environment, for example when testing for the presence or absence of nucleic acids, such as microbial nucleic acids. The present invention is therefore useful in detecting viruses, bacteria and fungi, for example from a sample (such as a swab) obtained from a surface. The invention can also be used to test liquids, such as water supplies.

The human or animal patient, or sample obtained from the environment, can be tested for a variety of diseases and conditions using the invention, for example cancer, infection or genetic disorders.

Cancers include acute lymphoblastic leukemia, acute or chronic lymphocyctic or granulocytic tumor, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumor, giant cell tumor, glioblastoma multiforma, hairy-cell tumor, head cancer, hyperplasia, hyperplastic corneal nerve tumor, in situ carcinoma, intestinal ganglioneuroma, islet cell tumor, Kaposi's sarcoma, kidney cancer, larynx cancer, leiomyomater tumor, liver cancer, lung cancer, lymphomas, malignant carcinoid, malignant hypercalcemia, malignant melanomas, marfanoid habitus tumor, medullary carcinoma, metastatic skin carcinoma, mucosal neuromas, mycosis fungoide, myelodysplastic syndrome, myeloma, neck cancer, neural tissue cancer, neuroblastoma, osteogenic sarcoma, osteosarcoma, ovarian tumor, pancreas cancer, parathyroid cancer, pheochromocytoma, polycythemia vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

Infections include bacterial, viral, fungal and parasitic infections. Bacterial infections include *Bacillus, bartonella, Bordetella, borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio* and *Yersinia* infections. Viral infections include alphavirus, enterovirus, flavivirus, hepatitis A virus, hepatitis B virus, hepatitis C virus, hepatitis E virus, deltavirus, cytomegalovirus, herpes virus, lentivirus, dengue virus, Epstein-Barr virus, HIV, HPV, pneumovirus, influenza virus, arenavirus, norovirus, morbillivirus, cardiovirus, rubulavirus, rabies virus, rotavirus, rubella virus, Venezuelan equine encephalitis virus, western equine encephalitis virus, west nile virus, yellow fever virus and zika virus infections. Fungal infections include athlete's foot (*Tinea pedis*), nail infections (*Tinea unguium*), ringworm, intertrigo, pituriasis *versicolor* (*Tinea versicolor*) infections and thrush (*Candida albicans*). Parasitic infections include *Entamoeba histoloitica, Giardia lamblia, Cryptosporidium parvum, Trichomonas vaginalis, Plasmodium malariae, Toxoplysma gondii, Pneumocystis jiroveci, Trypanosoma cruzi, Trypanosoma gambiense, Leishmania donovani, Diphyllobothrium latum, Echinococcus granulosus, Taenia saginata, Taenia solium, Schistosoma mansoni, Clonorchis sinensis, Paragonimus westermani, Ancylostoma duodenale, Ascaris lumbricoides, Enterobius vermicularis, Strogyloides stercoralis, Trichinella spirallis, Trichuris trichiura, Dracunculus medineinsis, Loa Ioa, Onchocerca volvulus, Wuchereria bancrofti, Toxocara canis, Pediculus humanus, Dermetobia huminis, Sarcoetes scabiei, Dermacentor* and *Latrodectus mactans* infections.

Genetic disorders include 22q11.2 deletion syndrome, Angelman syndrome, Canavan disease, Charcot-Marie-Tooth disease, Cri du chat, cystic fibrosis, Down's syndrome, Duchenne muscular dystrophy, haemochromatosis, haemophilia, Klinefelter syndrome, neurofibromatosis, phenylketonuria, polycystic kidney disease, Prader-Willi syndrome, sickle-cell disease, spinal muscular atrophy, Tay-Sachs disease and Turner syndrome. Of particular relevance is Down's syndrome and other aneuploidies, as the present invention can be used to detect such diseases in a sample obtained from a pregnant female, in particular a blood sample comprising cell-free fetal DNA (non-invasive prenatal testing, NIPT).

The NAOI may be at least 25 base pairs in length. In some embodiments, the NAOI may be from 25 to 100,000 base pairs in length, from 25 to 50,000 base pairs in length, from 25 to 10,000 base pairs in length, from 25 to 1000 base pairs in length, from 50 to 500 base pairs in length in length, from 100 to 250 base pairs in length, or from 100 to 200 base pairs in length. In order for the NAOI to be labelled and sequenced, the NAOI may be fragmented to an appropriate size (for example between 100 and 200 base pairs in length). Indeed, the NAOI may be an entire genome that is fragmented to an appropriate length to allow labelled and sequencing to take place. As discussed above, the NAOI may be from any suitable source, including a human, plant or microbial source, depending on the method being undertaken. Most commonly, the NAOI will be a human NAOI. A sample comprising NAOIs may comprise a mixture of NAOIs from a plurality of different sources.

In one embodiment, the NAOI is up to 50,000, up to 10,000, up to 5,000, up to 1,000, up to 500, up to 300, up to 250, up to 200, up to 180, up to 160, up to 140, up to 120, up to 100, up to 80, or up to 75 nucleotides in length. In one embodiment, the NAOI is from about 10 to about 10,000 nucleotides, about 10 to about 5,000 nucleotides, about 10 to about 3,000 nucleotides, about 10 to about 1,500 nucleotides about 10 to about 800 nucleotides about 10 to about 600 nucleotides about 10 to about 300 nucleotides, about 50 to about 250 nucleotides, about 100 to about 200 nucleotides, or about 100 to about 150 nucleotides in length.

The NAOI may be single stranded or double stranded. The NAOI may be a viral nucleic acid, microbial nucleic acid or genomic nucleic acid.

The NAOI can be DNA, RNA or cDNA. In one embodiment, the NAOI may be DNA obtained by reverse transcriptase of RNA. Accordingly, the method may comprise converting an RNA sequence to a DNA sequence to obtain the NAOI, optionally using a reverse transcriptase.

The NAOI may be a cell-free DNA (cfDNA), in particular a circulating tumour DNA (ctDNA) or circulating foetal DNA (cfDNA). Of course, ctDNA is of particular interest in embodiments relating to cancer diagnosis, prognosis or treatment. cfDNA is of particular interest in embodiment relating to non-invasive prenatal testing (NIPT).

The invention also provides a method for determining the sequence of a nucleic acid of interest, the method comprising:
 a. providing a pool of labelled NAOIs, wherein the labelled NAOIs have been labelled by a method of labelling NAOIs of the invention;
 b. amplifying the tagged nucleic acid of interest; and
 c. determining the sequence of the nucleic acid of interest.

The invention also provides a method for determining the sequence of a nucleic acid of interest, the method comprising:
 a. providing a sequence read prepared by labelling and subsequent amplification of NAOIs according to a method of labelling NAOIs of the invention as described herein; and
 b. determining the sequence of the nucleic acid of interest.

The invention also provides sequencing reads obtained according to any such method of determining the sequence of a nucleic acid of interest.

There is therefore provided a method of testing for a disease, condition or organism, comprising sequencing a NAOI according to a method of the invention as disclosed herein and determining the presence or absence of the disease, condition or organism by comparing the sequence of the nucleic acid of interest with a reference. The invention also provides a method for testing for a disease, condition or organism, the method comprising:
 a. providing a pool of labelled NAOIs, wherein the labelled NAOIs have been labelled by a method of labelling NAOIs of the invention;
 b. amplifying the tagged nucleic acid of interest;
 c. determining the sequence of the nucleic acid of interest; and
 d. determining the presence or absence of the disease, condition or organism by comparing the sequence of the nucleic acid of interest with a reference, e.g. a reference sequence.

The invention also provides a method for testing for a disease, condition or organism, the method comprising:
 a. providing an amplicon prepared by labelling and subsequent amplification of NAOIs according to a method of labelling NAOIs of the invention as described herein;
 b. determining the sequence of the nucleic acid of interest; and
 c. determining the presence or absence of the disease, condition or organism by comparing the sequence of the nucleic acid of interest with a reference, e.g. a reference sequence.

The reference may be the sequence of a NAOI that is associated with the disease, condition or organism. The sample may be a patient sample or a sample obtained from the environment, for example the source of the sample is being tested for the presence of a particular organism.

The present invention also provides a method of sequencing a NAOI, the method comprising the steps of:
 a. providing a sample from a patient, said sample comprising a plurality of NAOIs, wherein the NAOIs are cell-free DNA (cfDNA) molecules;
 b. labelling a plurality of the NAOIs according to a method of the invention as described herein; and
 c. sequencing the labelled NAOIs.

The methods of the invention may further comprise a step of determining the presence or absence of a NAOI in the sample, or the presence or absence of a genetic alteration (e.g., mutation or variant) in the nucleic acid of interest. The step of obtaining the sample may be a step of the method, or alternatively the method may be carried out using a sample previously obtained from a patient.

In one embodiment of the invention, the method may comprise:
  a) extracting cfDNA molecules from a patient sample;
  b) optionally processing the cfDNA molecules by end-repairing, 5'-phosporylating and/or 3' A-tailing the cfDNA molecules;
  c) attaching the oligonucleotides of the invention to one or both ends of the cfDNA molecules;
  d) amplifying the cfDNA molecules obtained from step (c) using PCR;
  e) enriching the amplified cfDNA molecules using target enrichment for a region or sequence of interest, for example by in-situ hybridisation;
  f) optionally further amplifying the enriched cfDNA molecules obtained from step (e); and
  g) sequencing the cfDNA molecules obtained from step (f).

The method may further comprise:
  h) obtaining the sequence reads from step (g)
  i) grouping the sequence reads:
    I. based on the sequence of the NAOI; and/or
    II. based on the sequence of the PCR cycle counter (if used); and
  j) obtaining consensus sequences for the cfDNA molecules.

In one specific embodiment of the invention, the method may comprise:
  a) extracting cfDNA molecules from a patient sample, wherein the patient sample comprises plasma;
  b) optionally quantifying the cfDNA molecules;
  c) processing the cfDNA molecules by end-repairing, 5' phosphorylating and/or 3' A-tailing;
  d) attaching the oligonucleotides of the invention to one or both ends of the cfDNA molecules, wherein the oligonucleotides are Y-stem adapters (i.e. the comprise an asymmetric portion to differentially label the two strands of the cfDNA);
  e) purifying the mixture to enrich for cfDNA molecules having one or more oligonucleotides attached;
  f) amplifying the NAOIs by PCR using primers targeted to the attached oligonucleotides, optionally wherein this step of amplification attaches universal primer sites, sequencing adaptors, and/or sample index sequences;
  g) purifying the mixture to enrich for amplified cfDNA molecules and/or enriching the amplified cDNA molecules using target enrichment for a region or sequence of interest, for example by in-situ hybridisation;
  h) optionally amplifying the enriched product using PCR; and
  i) sequencing the amplified product from step (j) using paired-end sequencing The method may further comprise:
  j) obtaining the sequence reads from step (i)
  k) grouping the sequence reads:
    i. based on the sequence of the NAOI and/or
    ii. based on the sequence of the PCR cycle counter (if used); and
  l) obtaining consensus sequences for the cfDNA molecules.

Methods provided herein include a method of diagnosing cancer, a method of determining cancer prognosis, a method of determining cancer remission or relapse, a method of detecting progression of cancer, or a method of determining the presence or absence of residual cancer, wherein the cfDNA is circulating tumour DNA (ctDNA) and the method further comprises determining the presence or absence of a genetic alteration in the ctDNA. In such methods, the NAOI is contained within or derived from a patient sample. The sample is obtained from a patient that has, is suspected of having, or has had, cancer. Alternatively, there may be no reason to suspect the patient has cancer, since the present method may be used for early detection of cancer. The present invention therefore provides:

(I) A method of diagnosing cancer or a method of detecting cancer mutations, comprising:
    a. providing a sample from a patient, said sample comprising a plurality of cfDNA molecules;
    b. determining the sequence of one or more of the cfDNA molecules according to a method of the invention as described herein;
    c. determining the presence or absence of one or more genetic alterations in the cfDNA molecules; and
    d. determining the presence or absence of cancer or cancer mutations based on the presence or absence respectively of the one or more genetic alterations.

(II) A method of determining cancer remission or relapse, comprising:
    a. providing a sample from a patient, said sample comprising a plurality of cfDNA molecules;
    b. determining the sequence of one or more of the cfDNA molecules according to a method of the invention as described herein;
    c. determining the presence or absence of one or more genetic alterations in the cfDNA molecules; and
    d. determining cancer remission or relapse based on the absence (or decrease in frequency of) or presence respectively of the one or more genetic alterations.

(III) A method of detecting progression of cancer, comprising:
    a. providing a sample from a patient, said sample comprising a plurality cfDNA molecules;
    b. determining the sequence of one or more of the cfDNA molecules according to a method of the invention as described herein;
    c. determining the presence or absence of one or more genetic alterations in the cfDNA molecules, or determining a change in the abundance of the one or more genetic alterations;
    d. optionally comparing the results from step (c) to the results for the same patient using a sample obtained at a previous point in time; and
    d. determining a progression of cancer based on the presence or absence of the one or more genetic mutations, or based on a change in the abundance of the one of more genetic alterations.

(IV) A method of determining the presence of residual cancer, comprising:
    a. providing a sample from a patient, said sample comprising a plurality cfDNA molecules;
    b. determining the sequence of one or more of the cfDNA molecules according to a method of the invention as described herein;
    c. determining the presence or absence of one or more genetic alterations in the cfDNA molecules; and
    d. determining the presence of residual cancer based on the presence or absence of the one or more genetic alterations.

The above methods may be carried out on patients that are undergoing or have undergone cancer treatment. Alternatively, the above methods may be determinative in the treatment regimen for a cancer patient. For example, progression of cancer may be a worsening or improvement. If a worsening of cancer is detected, the patient may be treated with a different or more aggressive chemotherapy and/or radiotherapy. If a sufficient improvement is detected, treatment may be ended. To determine a progression of cancer, it may be possible to analyse only one sample from a patient. For example, a genetic alteration (such as a cancer mutation) may be detected that is indicative of late stage or aggressive cancer. Alternatively, the results may be compared with a sample obtained from the same patient at an early point in time. For example, the earlier sample may have been obtained from the same patient prior to onset or diagnosis of cancer. Alternatively, the earlier sample may have been obtained from the same patient prior to or at an earlier stage of treatment. In this way, the progression of cancer in a patient can be measured by carrying out an analysis on two or more samples obtained from a patient at different points in time.

There is therefore also provided a method of treating cancer, comprising treating a patient for cancer, wherein the patient has been determined as having cancer or at risk of a worsening of cancer or of cancer remission or relapse using a method of the invention.

In one embodiment, the method of treatment comprises:
a. providing a sample from a patient, said sample comprising a plurality of cfDNA molecules;
b. determining the sequence of one or more of the cfDNA molecules according to a method of the invention as described herein;
c. determining the presence or absence of one or more genetic alterations in the cfDNA molecules;
d. selecting a cancer treatment regimen for the patient according to the presence or absence of a genetic alteration in the cell-free nucleic acid molecules; and
e. administering said cancer treatment regimen to the patient when one or more genetic alterations are detected.

Such a method may alternatively comprise:
a. determining the presence or absence of one or more genetic alterations in a library of sequence reads, the sequence reads having been obtained according to one of the methods of the invention described herein;
b. selecting a cancer treatment regimen for a patient according to the presence or absence of a genetic alteration in the cell-free nucleic acid molecules; and
c. administering said cancer treatment to the patient when one or more genetic alterations are detected.

The present invention also provides a method of determining a treatment regimen, such as a cancer treatment regimen, for a patient, for example a cancer patient or a patient suspected of having cancer, comprising:
a. providing a sample from a patient, said sample comprising one or more cell-free nucleic acid molecules
b. determining the sequence of one or more of the cell-free nucleic acid molecules according to a method of the invention as described herein;
c. determining the presence or absence of a genetic alteration in the cell-free nucleic acid molecules; and
d. selecting a treatment regimen for the patient according to the presence or absence of a genetic alteration in the cell-free nucleic acid molecules.

Such a method may alternatively comprise:
a. determining the presence or absence of one or more genetic alterations in a library of sequence reads, the sequence reads having been obtained according to one of the methods described herein; and
b. selecting a treatment regimen for the patient according to the presence or absence of a genetic alteration in the library of sequence reads.

In some embodiments, the methods include the step of administering treatment.

In embodiments relating to treatment of diseases (such as cancer) or selecting a treatment regimen for a disease (such as cancer), the treatment may be based on the results of the genetic analysis. In some embodiments, the presence of a genetic alteration may be indicative of disease, or indicative of resistance or susceptibility to certain treatments. In some embodiments, the frequency of a genetic alteration may be indicative of disease, or indicative of resistance or susceptibility to certain treatments. In such embodiments, the method may further comprise the step of comparing the results of the genetic analysis to a reference (such as a healthy control or a control taken from the same patient at a different point in time). The skilled person would be able to interpret the results of the genetic analysis, depending on the context. Additionally or alternatively, the methods may include conducting an analysis on two or more samples obtained from the same patient at different points in time. In this way, disease progress and the success or failure of treatments can be monitored.

The present invention also provides a method of predicting a patient's responsiveness to a cancer treatment, comprising
a. providing a sample from a patient, said sample comprising a plurality of cell-free DNA (cfDNA) molecules;
b. determining the sequence of one or more of the cfDNA molecules according to a method of the invention as described herein;
c. determining the presence or absence of a genetic alteration; and
d. predicting a patient's responsiveness to a cancer treatment according to the presence or absence of a genetic alteration.

Such a method may alternatively comprise:
a. determining the presence or absence of one or more genetic alterations in a library of sequence reads, the sequence reads having been obtained according to one of the methods described herein; and
b. predicting a patient's responsiveness to a cancer treatment according to the presence or absence of a genetic alteration in the library of sequence reads.

The treatment to be administered will generally be chemotherapy and/or radiotherapy, including targeted cancer therapies. The specific treatment regimen may depend on the type of cancer that is detected. For example, some genetic alterations (e.g., mutations) may be indicative of a particular resistance or susceptibility to certain treatments, and the treatment regimen can be designed accordingly.

The genetic alterations being detected are not limited in the present invention and are known and understood by the skilled person. Indeed, methods of the present invention can be used to detect new or existing genetic alterations and associate those alterations with particular cancers or particular patient outcomes, for example susceptibility or resistance to particular treatment regimens.

Generally, the type of genetic alteration or genetic variation being detected will depend on the context. For example, an alteration, variation or mutation that affects the amount or activity of the gene or gene product, as compared to the normal or wild-type gene. The alteration can be in amount, structure, and/or activity in a diseased tissue or cell (e.g., cancer tissue or cell), as compared to its amount, structure, and/or activity, in a normal or healthy tissue or cell (e.g., a control), and is associated with a disease state, such as cancer. Alternatively, the genetic alteration might be indicative of a genetic disease.

An alteration might have an altered nucleotide sequence (e.g., a mutation), amino acid sequence, chromosomal translocation, intra-chromosomal inversion, copy number, expression level, protein level, protein activity, or methylation status, in a cancer tissue or cancer cell (or in cell free DNA arising from cancer cells), as compared to a normal, healthy tissue or cell. Exemplary alterations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene. In certain embodiments, the alteration(s) is detected as a rearrangement, e.g., a genomic rearrangement comprising one or more introns or fragments thereof (e.g., one or more rearrangements in the 5'- and/or 3'-UTR). In certain embodiments, the alterations are associated (or not associated) with a phenotype, e.g., a cancerous phenotype (e.g., one or more of cancer risk, cancer progression, cancer treatment or resistance to cancer treatment). In one embodiment, the alteration is associated with one or more of: a genetic risk factor for cancer, a positive treatment response predictor, a negative treatment response predictor, a positive prognostic factor, a negative prognostic factor, or a diagnostic factor.

Alterations and mutations that can be detected using the methods of the invention may be or may occur in or at: a single nucleotide position; an intragenic region or an intergenic region; an exon or an intron, or a fragment thereof; a coding region or a non-coding region; a promoter, an enhancer, a 5' untranslated region (5' UTR), or a 3' untranslated region (3' UTR), or a fragment thereof; a cDNA or a fragment thereof; a single nucleotide polymorphism (SNP, also referred to as a single nucleotide variant, SNV); a somatic mutation, a germ line mutation or both; a point or a single mutation; a deletion mutation; an in-frame deletion, an intragenic deletion, a full gene deletion; an insertion mutation; an intragenic insertion; an inversion mutation; an intra-chromosomal inversion; a linking mutation; a linked insertion mutation; an inverted duplication mutation; a tandem duplication; an intrachromosomal tandem duplication; a translocation; a chromosomal translocation, a non-reciprocal translocation; a rearrangement; a genomic rearrangement; a rearrangement of one or more introns, or a fragment thereof; a rearranged intron; a gene fusion; a copy number variation (CNV); or a combination thereof.

The present invention includes methods of determining alterations in copy number, the method comprising determining the sequences of a pool of NAOIs according to a method described herein, wherein each of the NAOIs in a pool represent a given region of a reference genome, quantifying the relative frequency at which each region of the reference genome is represented in the pool of NAOIs, thereby identifying changes in copy number for a region of the reference genome.

In embodiments of the invention relating to cancer, the genetic alteration will be a genetic cancer alteration, such as a cancer mutation, which is associated with cancer, or predictive of responsiveness or non-responsiveness to anti-cancer therapeutics.

The method of the present invention may be conducted on one or more target genes from which ctDNAs may be derived. In one embodiment, the target gene is selected from the group consisting of AKT1, BRAF, CCND1, CDKN2A, CTNNB1, EGFR, ERBB2, ESR1, FGFR1, FGFR2, FGFR3, GATA3, GNA11, GNAQ, GNAS, HRAS, IDH1, IDH2, KIT, KRAS, MAP2K1, MET, MYC, NFE2L2, NRAS, NTRK1, NTRK3, PDGFRA, PIC3CA, PPP2R1A, PTEN, STK11, TP53 and U2AF1, although other genes could be targeted. Specific regions of the genome may be targeted in the method by performing a target enrichment step to amplify a target or region of interest prior to ligation of the spacer oligonucleotides. Alternatively, a target enrichment step may be undertaken after amplification of the ligated NAOIs.

Cancer progression is associated with accumulation of genetic alterations in cells. Alterations in tumor suppressor genes and oncogenes accumulate during tumor progression and may correlate with the clinical aggressiveness of cancer. A number of genes have been also identified that play a role in inducing or suppressing metastasis.

In one embodiment, methods of the invention can be used to target patient-specific mutations. As per, for example, Forshew et al., "Noninvasive identification and monitoring of cancer mutations by targeted deep sequencing of plasma DNA", 2012, Sci Transl Med., May 30; 4 (136): 136ra68, the contents of which are incorporated by reference herein, a tumour or plasma sample from a patient is sequenced, for example using a broad method such as whole genome, exome or cancer panel sequencing. A capture panel targeting patient-specific somatic mutations identified during this sequencing can then be generated. Optionally, this capture panel can be combined with a non-patient-specific panel. Importantly the capture panel can include both driver and passenger mutations. A driver mutation is causally implicated in oncogenesis. It has conferred growth advantage on the cancer cell and has been positively selected in the microenvironment of the tissue in which the cancer arises. A driver mutation need not be required for maintenance of the final cancer. A passenger mutation has not contributed to cancer development. Passenger mutations are found within cancer genomes because somatic mutations without functional consequences often occur during cell division. Thus, a cell that acquires a driver mutation will typically already have biologically inert somatic mutations within its genome. These will be carried along in the clonal expansion that follows and therefore will be present in all cells of the final cancer.

The capture panel can then be used with the methods of the invention described herein to diagnose, monitor or characterise a cancer in a patient. By screening for a large number of mutations previously identified in the patient there is an improved ability to detect cancer DNA and a more accurate ability to quantify average levels, since even if the tumour evolves it is unlikely that it will lose all mutations. Equally, even if less than 1 copy of the cancer genome is analysed by screening for multiple changes, detection is still possible using the methods of the invention as the error correction aspect provides methods with significantly increased accuracy over the prior art.

Accordingly, in a further aspect of the invention there is provided a method of monitoring disease progression of cancer in an individual, said method comprising
  (a) determining according to a method of the invention as described herein the presence or absence of one or more genetic alterations associated with a cancer in body fluid samples obtained from said individual at a plurality of time points following diagnosis of said individual with cancer;

(b) comparing the results obtained at each time point in order to determine the progression of the cancer in said individual; wherein the same or an increase in genetic alteration levels between samples taken at different time points indicates an increase in cancer burden, and wherein a decrease in cancer alteration levels between samples taken at different time points indicates cancer regression.

In one embodiment, the step of determining the presence or absence of one or more genetic alterations associated with cancer is carried out after initiation of treatment.

In some embodiments, the results are further compared with genetic alteration levels determined prior to initiation of treatment from an initial or primary sample of fluid or tissue obtained from the individual following diagnosis with cancer. For example an initial genetic alteration profile may be established from a tumor tissue sample obtained from the individual and/or from a blood sample.

The methods of the present invention also allow detection of minimal residual disease in patients. For example, following treatment for cancer, the methods of the present invention may be used to detect residual disease using a sample obtained from the patient. The potentially for relapse can therefore be detected early and appropriate additional treatment steps be taken.

There is also provided a method of stratifying a microbial population, comprising:
a. obtaining a sample comprising a plurality of microbial nucleic acids of interest;
b. determining the sequence of one or more of the microbial nucleic acids of interest according to a method of the invention as described herein;
c. mapping the sequence reads obtained in step b to a reference genome or genomes; and
d. stratifying the microbial population according to the identified microbes.

The present invention further provides a mixture or composition comprising a pool of oligonucleotides of the invention and one or more nucleic acids of interest. In some embodiments, the adaptors are attached to the nucleic acids of interest. The nucleic acids of interest may be from 25 to 100,000 base pairs in length, from 25 to 50,000 base pairs in length, from 25 to 10,000 base pairs in length, from 25 to 1000 base pairs in length, from 50 to 500 base pairs in length, from 100 to 250 base pairs in length, or from 100 to 200 base pairs in length. In some embodiments, the nucleic acids of interest are double-stranded, for example double-stranded cfDNA obtained from a patient. The cfDNA may be ctDNA.

The invention also provides kits. The kit of parts comprises oligonucleotide pools of the invention and instructions for use. The kit may also comprise one or more nucleotides in solution, for example, A, T, C and G nucleotides in solution. The adaptors and nucleotides in solution are disposed in separate containers. In some embodiments, the different types of nucleotides are disposed in separate containers.

In some embodiments of the invention, the kit further comprises enzymatic means for ligation of nucleic acids. The enzymatic means for ligation of nucleic acids can be a ligase, for example a DNA ligase, such as T4 DNA ligase. The kit may also (or alternatively) comprise enzymatic means for polymerisation of nucleic acids. The enzymatic means for polymerisation of nucleic acids can be a polymerase, such as a DNA polymerase, for example Taq DNA polymerase.

In some embodiments of the invention, each component of the kit is disposed in separate container, with one container comprising the pool of adaptors and optionally the nucleotides in solution (or the nucleotides in solution may be in a container or containers separate to the pool of extension adaptors).

The present invention provides methods for labelling a nucleic acid using a pool of oligonucleotides, usually double stranded oligonucleotides. Each oligonucleotide may comprise a universal priming site, a variable length spacer region and a filler region. The oligonucleotide may further comprise a PCR cycle counter generator region comprising at least one universal base and/or an asymmetric (i.e. non-complementary) portion. For example, the oligonucleotide may be an asymmetric adaptor comprising an asymmetric portion, a universal priming site, a spacer region comprising from 1 to 75 nucleotides, a filler region comprising from 1 to 20 nucleotides, and optionally a PCR cycle counter generator region comprising from 1 to 20 nucleotides including at least 2 universal bases.

Oligonucleotides are attached randomly to the NAOIs to randomly shift that start and/or stop read coordinates when the NAOI is subsequently sequenced.

The method may comprise:
2. providing a sample comprising a plurality of NAOIs, each having a natural start coordinate defined by the 5' end of the NAOI and a natural stop coordinate defined by the 3' end of the NAOI;
3. contacting the sample with a pool of double-stranded asymmetric oligonucleotides, the pool comprising oligonucleotides having at least 5 different lengths, each oligonucleotide in the pool comprising a universal priming site, a variable length spacer region, a filler region, and optionally a PCR cycle counter generator region;
4. randomly attaching an oligonucleotide from the pool to one or each end of a plurality of NAOIs to provide a plurality of labelled NAOIs, wherein attachment of the oligonucleotides to the plurality of NAOIs alters the number of base pairs of the NAOI that are obtained when the labelled NAOI is subsequently sequenced;
5. amplifying the labelled NAOIs;
6. sequencing the labelled NAOIs to provide a library of reads, each sequence read comprising an oligonucleotide-derived portion and a NAOI-derived portion;
7. grouping the reads according to the sequence obtained from the NAOI (i.e. the NAOI-derived portion of the sequence read);
8. determining a consensus sequence for each NAOI.

Preferred features for the second and subsequent aspects of the invention are as provided for the first aspect, mutatis mutandis.

The present invention will now be further described with reference to the following examples, which should not be construed as being limiting on the scope of the invention.

EXAMPLES

Example 1: Barcoding DNA 16,000 genomic input copies are made up to 50 µL by diluting in 10 mM Tris-HCl, pH 8. DNA is end repaired, 5' phosphorylated and 3' A-tailed using 3 µl NEBNext Ultra II End Prep Enzyme Mix and 7 µl NEBNext Ultra II End Prep Reaction Buffer in a total volume of 60 µL (NEBNext Ultra II DNA Library Prep Kit for Illumina (NEB: E7645S)). Reagents are mixed by pipetting up and down 10 times.

DNA is incubated on the thermocycler for 30 minutes at 20° C. followed by 30 minutes at 65° C., with the thermocycler lid temperature set to 75° C. Adapter ligation is performed by adding 30 µl NEBNext Ultra II Ligation Master mix, 1 µl NEBNext Ligation Enhancer and 2.5 µl Ligation adapters (stock concentration 90 µM). Samples are mixed by pipetting up and down 10 times. The reaction mixture is incubated on the thermocycler at 20° C. for 15 minutes with the thermocycler lid temperature switched off. At this stage samples can be stored at −20° C. overnight. A SPRI bead (Beckman Coulter) clean-up is performed at a 0.9× bead to sample ratio, following the manufacturers recommendations. DNA is eluted in 18 µl Tris-HCl pH 8. 16 µl of the eluate is recovered. The DNA is split into 4 reactions (4×4 L). To each 4 µL DNA, 6.25 µl KAPA HIFI HS URACIL+RM (Roche 07959052001), 0.25 µl primer (NEBNext i501 and i701 indexing primers mixed together at a final concentration of 50 µM of each primer. * See example PCR primer sequences below) and 2 µl nuclease free water are added. PCR amplification is performed using the following parameters: step1. 95° C. 3 min, step2. 98° C. 20 sec, step3. 62° C. 15 sec, step4. 72° C. 1 min, Cycle back to step2, 4 times for a total of 5 cycles, step5 72° C. 1 min, hold at 4° C. A SPRI bead (Beckman Coulter) clean-up is performed at a 0.9× bead to sample ratio, following the manufacturers recommendations. DNA is eluted in 18 µl Tris-HCl pH 8. Average library size is assessed using the Tapestation. The library is quantified using KAPA qPCR quantification, following the manufacturers recommendations (Roche: KK4873). The library is sequenced on the Next-Seq 500 illumina instrument, following the manufacturers recommendations.

Example 2: Barcoding DNA with Enrichment for Regions of Interest 16,000 genomic input copies are made up to 50 µL by diluting in 10 mM Tris-HCl, pH 8. DNA is end repaired, 5' phosphorylated and 3' A-tailed using 3 µl NEBNext Ultra II End Prep Enzyme Mix and 7 µl NEBNext Ultra II End Prep Reaction Buffer in a total volume of 60 µL (NEBNext Ultra II DNA Library Prep Kit for Illumina (NEB: E7645S)). Reagents are mixed by pipetting up and down 10 times. DNA is incubated on the thermocycler for 30 minutes at 20° C. followed by 30 minutes at 65° C., with the thermocycler lid temperature set to 75° C. Adapter ligation is performed by adding 30 µl NEBNext Ultra II Ligation Master mix, 1 µl NEBNext Ligation Enhancer and 2.5 µl Ligation adapters (stock concentration 90 M). Samples are mixed by pipetting up and down 10 times. The reaction mixture is incubated on the thermocycler at 20° C. for 15 minutes with the thermocycler lid temperature switched off. At this stage samples can be stored at −20° C. overnight. A SPRI bead (Beckman Coulter) clean-up is performed at a 0.9× bead to sample ratio, following the manufacturers recommendations. DNA is eluted in 18 µl Tris-HCl pH 8. 16 µl of the eluate is recovered. The DNA is split into 4 reactions (4×4 L). To each 4 µL DNA, 6.25 µl KAPA HIFI HS URACIL+RM (Roche 07959052001), 0.25 µl primer (NEBNext i501 and i701 indexing primers mixed together at a final concentration of 50 UM of each primer. * See example PCR primer sequences below)) and 2 µl nuclease free water are added. PCR amplification is performed using the following parameters: step1. 95° C. 3 min, step2. 98° C. 20 sec, step3. 62° C. 15 sec, step4. 72° C. 1 min, Cycle back to step2, 4 times for a total of 5 cycles, step5 72° C. 1 min, hold at 4° C. A SPRI bead (Beckman Coulter) clean-up is performed at a 0.9× bead to sample ratio, following the manufacturers recommendations. DNA is eluted in 18 µl Tris-HCl pH 8.

DNA is quantified using the Qubit fluorometer, following the manufacturers recommendations. Genomic DNA is enriched for regions of interest using xGen® Lockdown® probes and reagents form IDT, following the manufacturers recommendations. Average library size is assessed using the Tapestation. The library is quantified using KAPA qPCR quantification, following the manufacturers recommendations (Roche: KK4873). The library is sequenced on the Next-Seq 500 illumina instrument, following the manufacturers recommendations.

*Example PCR primer sequences:

```
                                                    (SEQ ID NO: 1)
I501: AATGATACGGCGACCACCGAGATCTACACTATAGCCTACACTC

TTTCCCTACACGACGCTCTTCCGATC*T (SEQ ID NO: 2)
I701: CAAGCAGAAGACGGCATACGAGATCGAGTAATGTGACTGGAGT

TCAGACGTGTGCTCTTCCGATC*T
Underlined: Illumina TruSeq HT index sequence,
*phosphorothioate linkage)
```

---

What is claimed is:

1. A method of labelling a nucleic acid of interest (NAOI) in a sample from a patient, the method comprising:
   (a) contacting the sample comprising the NAOI with a pool of oligonucleotides, wherein each oligonucleotide in the pool of oligonucleotides comprises a variable length region and a sequencing primer site;
   (b) attaching an oligonucleotide from the pool of oligonucleotides on to one or each end of the NAOI, thereby creating a tagged NAOI;
   (c) sequencing the tagged NAOI, wherein the sequencing comprises sequencing both the variable length region of the oligonucleotide and the sequence of the NAOI, such that the sequence of the tagged NAOI comprises a modified read start or stop coordinate from the sequence of the NAOI;
   (d) grouping the sequence of the tagged NAOI with the sequences of a plurality of tagged NAOIs from the sample, wherein the plurality of tagged NAOIs from the sample have a variable length region that is the same length as the variable length region in the tagged NAOI and further have an identical or substantially identical sequence to the tagged NAOI; and
   (e) determining a presence or an absence of a genetic alteration in the NAOI based on the grouped sequences.

2. The method of claim 1, wherein the sample is a blood sample from the patient.

3. The method of claim 1, wherein the NAOI is between 100 and 250 nucleotides in length.

4. The method of claim 1, wherein the NAOI is a cell-free deoxyribonucleic acid (DNA).

5. The method of claim 3, wherein the patient has cancer and wherein the NAOI is circulating tumor DNA.

6. The method of claim 5, wherein the genetic alteration is a previously identified genetic alteration from the patient's cancer.

7. The method of claim 1, wherein the sequencing further comprises next-generation sequencing.

8. The method of claim 7, wherein the sequencing further comprises sequencing both a 5' end and a 3' end of the tagged NAOI.

9. The method of claim 1, further comprising enriching the sample for the NAOI.

10. The method of claim 9, wherein enriching the sample for the NAOI comprises targeted amplification.

11. The method of claim 1, wherein the variable length region is between 1 and 75 nucleotides.

12. The method of claim 1, wherein the genetic alteration is present at an allele frequency of 1% or below.

13. The method of claim 1, wherein the variable length region comprises at least 5 different lengths.

14. The method of claim 1, wherein attaching the oligonucleotide from the pool of oligonucleotides is performed by ligation or polymerase chain reaction (PCR).

15. The method of claim 1, wherein each oligonucleotide in the pool of oligonucleotides further comprise a ligation moiety.

16. The method of claim 1, wherein grouping the sequences further comprises grouping the sequences according to the modified read start or stop coordinate.

17. The method of claim 1, further comprising determining a consensus sequence for the tagged NAOI.

18. A method of preparing a preparation useful for detecting cancer mutations in a sample from a cancer patient and labelling a plurality of nucleic acids of interest (NAOIs) in the sample from the cancer patient, the method comprising:

(a) contacting a sample comprising a plurality of nucleic acids of interest (NAOIs) with a pool of oligonucleotides, wherein the pool of oligonucleotides comprises oligonucleotides having a variable length region and a sequencing primer site, wherein each NAOI of the plurality of NAOIs comprises cell-free deoxyribonucleic acid (DNA) and is between 100 and 250 nucleotides in length;

(b) attaching oligonucleotides from the pool of oligonucleotides on to one or each end of the NAOIs, thereby tagging the NAOIs;

(c) sequencing the tagged NAOIs, wherein the sequencing comprises sequencing both the variable length region of the oligonucleotides and the sequence of the NAOIs, such that the sequence of each tagged NAOI comprises a modified read start or stop coordinate from the sequence of its original NAOI;

(d) grouping the sequences of the tagged NAOIs based on a length of the variable length region and a degree of similarity between the NAOIs; and (e) determining a presence or an absence of a genetic alteration associated with cancer based on the grouped sequences.

19. The method of claim 18, wherein the genetic alteration associated with cancer comprises a genetic alteration previously identified in the cancer patient.

20. The method of claim 19, wherein the method is performed after initiating a treatment.

* * * * *